(12) United States Patent
Appel et al.

(10) Patent No.: US 6,856,132 B2
(45) Date of Patent: Feb. 15, 2005

(54) METHOD AND APPARATUS FOR SUBTERRANEAN FORMATION FLOW IMAGING

(75) Inventors: Matthias Appel, Norwich (GB); John Justin Freeman, Houston, TX (US); Mario Winkler, Houston, TX (US); Bernhard Peter Jakob Blumich, Roetgen (DE)

(73) Assignee: Shell Oil Company, Houston, TX (US)

( * ) Notice: Subject to any disclaimer, the term of this patent is extended or adjusted under 35 U.S.C. 154(b) by 8 days.

(21) Appl. No.: 10/291,963

(22) Filed: Nov. 8, 2002

(65) Prior Publication Data

US 2004/0090230 A1 May 13, 2004

(51) Int. Cl.⁷ .................................. G01V 3/00
(52) U.S. Cl. ........................ 324/303; 324/306
(58) Field of Search ........................... 324/303, 306, 324/307, 309, 300

(56) References Cited

U.S. PATENT DOCUMENTS

| | | | |
|---|---|---|---|
| 3,611,118 A | 10/1971 | Youngblood | 324/0.5 |
| 3,657,730 A | 4/1972 | Robinson | 324/0.5 |
| 3,784,898 A | 1/1974 | Darley | 324/0.5 |
| 4,035,718 A | 7/1977 | Chandler | 324/0.5 |
| 4,156,177 A | 5/1979 | Coates | 324/6 |
| 4,175,251 A | 11/1979 | Chandler | 324/303 |
| 4,528,508 A | 7/1985 | Vail, III | 324/303 |
| 4,644,283 A | 2/1987 | Vinegar et al. | 324/376 |
| 4,710,713 A | 12/1987 | Strikman | 324/303 |
| 4,717,876 A | 1/1988 | Massi et al. | 324/303 |
| 4,717,877 A | 1/1988 | Taicher et al. | 324/303 |
| 4,719,423 A | 1/1988 | Vinegar et al. | 324/303 |
| 4,728,892 A | 3/1988 | Vinegar et al. | 324/309 |
| 4,739,255 A | 4/1988 | Hagiwara | 324/152 |
| 4,743,854 A | 5/1988 | Vinegar et al. | 324/366 |
| 4,745,802 A | 5/1988 | Purfurst | 73/155 |
| 4,773,264 A | 9/1988 | Herron | 73/152 |
| 4,884,455 A | 12/1989 | Vinegar et al. | 73/798 |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg | 324/303 |
| 5,114,567 A | 5/1992 | DiFoggio | 208/401 |
| 5,153,514 A | 10/1992 | Griffin et al. | 324/303 |
| 5,212,447 A | 5/1993 | Paltiel et al. | 324/300 |
| 5,247,830 A | 9/1993 | Goode | 73/155 |
| 5,280,243 A | 1/1994 | Miller | 324/303 |
| 5,291,137 A | 3/1994 | Freedman | 324/303 |
| 5,306,640 A | 4/1994 | Vinegar et al. | 436/29 |
| 5,309,098 A | 5/1994 | Coates et al. | 324/303 |
| 5,363,041 A | 11/1994 | Sezginer | 324/303 |
| 5,376,884 A | 12/1994 | Sezginer | 324/303 |
| 5,381,092 A | 1/1995 | Freedman | 324/303 |
| 5,389,877 A | 2/1995 | Sezginer et al. | 324/303 |
| 5,412,320 A | 5/1995 | Coates | 324/303 |
| 5,428,291 A | * 6/1995 | Thomann et al. | 324/303 |
| 5,432,446 A | 7/1995 | MacInnis et al. | 324/303 |
| 5,451,873 A | 9/1995 | Freedman et al. | 324/303 |

(List continued on next page.)

Primary Examiner—Louis Arana

(57) ABSTRACT

The present invention relates to a method and apparatus for measuring a property relating to fluid flow in an earth formation, more specifically to directly measuring formation permeability and other fluid characteristics. The present invention provides a method for determining the permeability of a hydrocarbon bearing earth formation, which method comprises the steps of: locating a tool at a selected position in a borehole penetrating the earth formation; inducing a flow of fluid within the earth formation to said tool; creating at least two MRI images of said fluid while flowing within the earth formation to said tool, said at least two images being created at different times; determining displacement of said fluid within the earth formation between said different times, using the at least two MRI images.

17 Claims, 16 Drawing Sheets

U.S. PATENT DOCUMENTS

| | | | |
|---|---|---|---|
| 5,486,761 A | 1/1996 | Sezginer | 324/303 |
| 5,486,762 A | 1/1996 | Freedman et al. | 324/303 |
| 5,497,087 A | 3/1996 | Vinegar et al. | 324/303 |
| 5,498,960 A | 3/1996 | Vinegar et al. | 324/303 |
| 5,517,115 A | 5/1996 | Prammer | 324/303 |
| 5,557,200 A | 9/1996 | Coates | 324/303 |
| 5,557,201 A | 9/1996 | Kleinberg et al. | 324/303 |
| 5,585,720 A | 12/1996 | Edwards | 324/309 |
| 5,596,274 A | 1/1997 | Sezginer | 324/303 |
| 5,629,623 A | 5/1997 | Sezginer et al. | 324/303 |
| 5,633,590 A | 5/1997 | Vail, III | 324/368 |
| 5,644,231 A | 7/1997 | Wignall | 324/303 |
| 5,680,043 A | 10/1997 | Hurlimann et al. | 324/303 |
| 5,696,448 A | 12/1997 | Coates et al. | 324/303 |
| 5,698,979 A | 12/1997 | Taicher et al. | 324/303 |
| 5,705,927 A | 1/1998 | Sezginer et al. | 324/303 |
| 5,710,511 A | 1/1998 | Taicher et al. | 324/303 |
| 5,712,566 A | 1/1998 | Taicher et al. | 324/303 |
| 5,757,186 A | 5/1998 | Taicher et al. | 324/303 |
| 5,764,058 A | 6/1998 | Itskovich et al. | 324/303 |
| 5,784,333 A | 7/1998 | Tang | 367/30 |
| 5,796,252 A | 8/1998 | Kleinberg et al. | 324/303 |
| 5,814,988 A | 9/1998 | Itskovich et al. | 324/303 |
| 5,828,214 A | 10/1998 | Taicher et al. | 324/303 |
| 5,834,936 A | 11/1998 | Taicher et al. | 324/303 |
| 5,914,598 A | 6/1999 | Sezginer et al. | 324/303 |
| 5,923,167 A | 7/1999 | Chang et al. | 324/303 |
| 5,936,405 A | 8/1999 | Prammer et al. | 324/303 |
| 5,959,453 A | 9/1999 | Taicher et al. | 324/303 |
| 5,977,768 A | 11/1999 | Sezginer et al. | 324/303 |
| 6,005,389 A | 12/1999 | Prammer | 324/303 |
| 6,018,243 A | 1/2000 | Taicher et al. | 324/303 |
| 6,023,163 A | 2/2000 | Flaum et al. | 324/303 |
| 6,023,164 A | 2/2000 | Prammer | 324/303 |
| 6,026,560 A | 2/2000 | Wignall | 29/607 |
| 6,032,101 A | 2/2000 | Freedman et al. | 702/8 |
| 6,040,696 A | 3/2000 | Ramakrishnan et al. | 324/303 |
| 6,047,239 A | 4/2000 | Berger et al. | 702/9 |
| 6,047,595 A | 4/2000 | Herron et al. | 73/152.05 |
| 6,049,205 A | 4/2000 | Taicher et al. | 324/303 |
| 6,051,973 A | 4/2000 | Prammer | 324/303 |
| 6,069,477 A | 5/2000 | Chen et al. | 324/303 |
| 6,069,479 A | 5/2000 | Taicher et al. | 324/309 |
| 6,072,314 A | 6/2000 | Oraby | 324/303 |
| 6,084,408 A | 7/2000 | Chen et al. | 324/303 |
| 6,088,656 A | 7/2000 | Ramakrishnan et al. | 702/13 |
| 6,094,048 A | 7/2000 | Vinegar et al. | 324/303 |
| 6,097,184 A | 8/2000 | Flaum | 324/303 |
| 6,107,796 A | 8/2000 | Prammer | 324/303 |
| 6,107,797 A | 8/2000 | Sezginer | 324/303 |
| 6,111,408 A | 8/2000 | Blades et al. | 324/303 |
| 6,111,409 A | 8/2000 | Edwards et al. | 324/303 |
| 6,115,671 A | 9/2000 | Fordham et al. | 702/8 |
| 6,118,272 A | 9/2000 | Taicher et al. | 324/303 |
| 6,119,777 A | 9/2000 | Runia et al. | 166/254.2 |
| 6,121,773 A | 9/2000 | Taicher et al. | 324/303 |
| 6,121,774 A | 9/2000 | Sun et al. | 324/303 |
| 6,133,734 A | 10/2000 | McKeon | 324/303 |
| 6,133,735 A | 10/2000 | Hurlimann et al. | 324/303 |
| 6,140,816 A | 10/2000 | Herron | 324/303 |
| 6,140,817 A | 10/2000 | Flaum et al. | 324/303 |
| 6,140,818 A | 10/2000 | Hurlimann | 324/303 |
| 6,147,489 A | 11/2000 | Freedman et al. | 324/303 |
| 6,518,758 B1 | 2/2003 | Speier et al. | 324/303 |
| 6,528,995 B1 | 3/2003 | Speier et al. | 324/303 |
| 6,531,869 B1 | 3/2003 | Speier et al. | 324/303 |
| 6,538,438 B1 | 3/2003 | Speier et al. | 324/303 |
| 2003/0052673 A1 | 3/2003 | Speier et al. | 324/303 |
| 2003/0052674 A1 | 3/2003 | Speier et al. | 324/303 |

\* cited by examiner

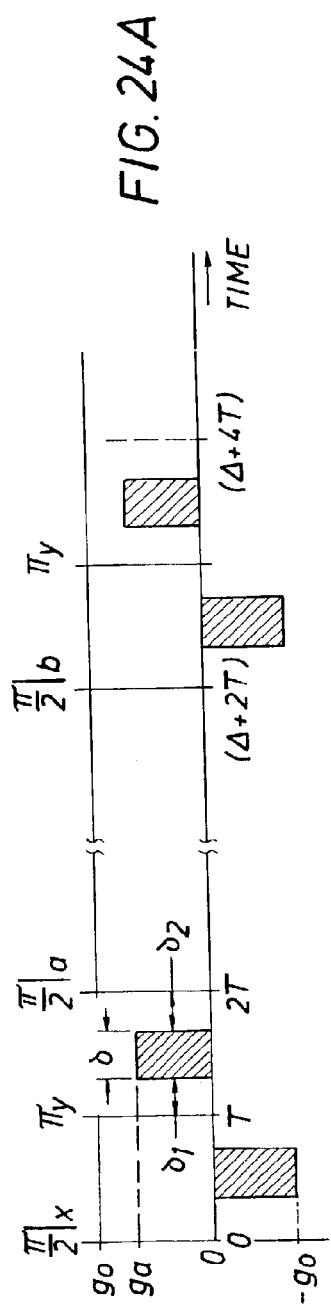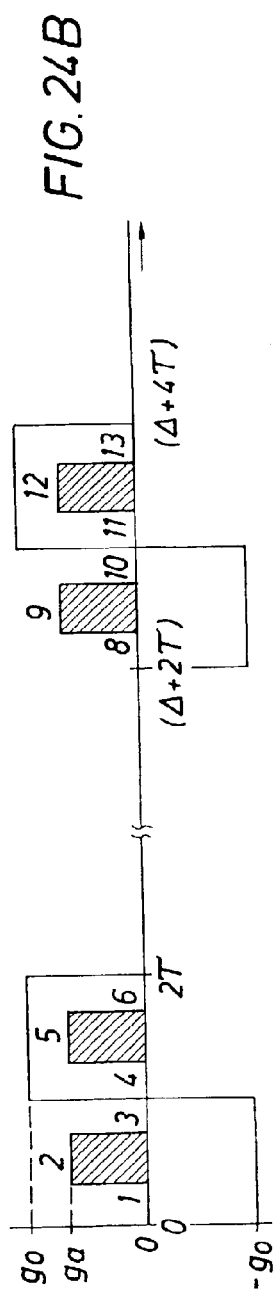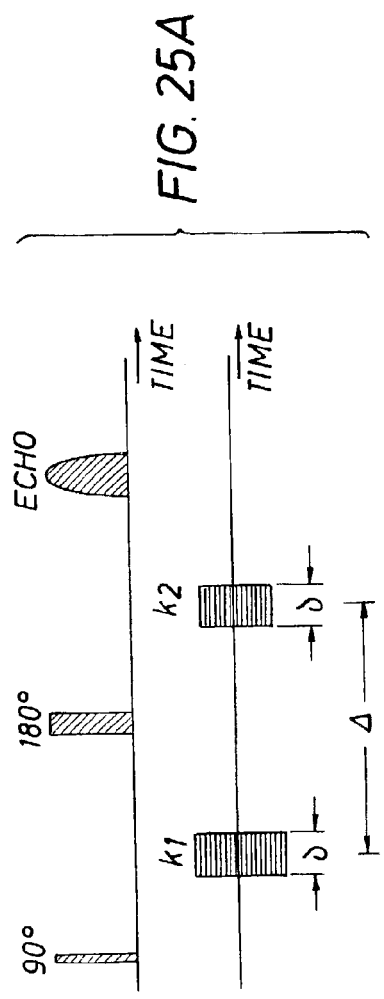

METHOD AND APPARATUS FOR SUBTERRANEAN FORMATION FLOW IMAGING

FIELD OF THE INVENTION

The present invention relates to an apparatus and techniques for determining characteristics of Earth formations surrounding a borehole and, more particularly, to an apparatus and method for nuclear magnetic resonance (NMR) borehole logging further being capable of magnetic resonance imaging (MRI) the formations surrounding the borehole and determine other formation characteristics such as porosity and permeability, as well as the characterization of fluids in the formation.

BACKGROUND OF THE INVENTION

A major goal in the evaluation of hydrocarbon bearing Earth formations is the accurate determination of the volumes of oil and water in the pore space of sedimentary rocks. Measurements made with signals from logging instruments have been used to obtain estimates of these volumes. The most credible measurement of producibility of the fluid volumes is to actually produce fluids from the formation; such as by using a drill stem test or by using a logging device that extracts fluids from the formations.

However, it is desirable to determine the nature of the earth formation and make estimates of the bulk volume of the fluids present in the formation, as well as their producibility, prior to undertaking the measures set forth above. Petrophysical parameters of a geological formation which are typically used to determine whether the formation will produce viable amount of hydrocarbons include the formation porosity, fluid saturation, the volume of the formation and its permeability. Formation porosity is the Dore volume per unit volume of formation; it is the fraction of the total volume of a sample that is occupied by pores or voids. The saturation of a formation is the fraction of its Dore volume occupied by the fluid of interest. Thus, water saturation is the fraction of the Dore volume that contains water. The water saturation of the formation can vary from 100 percent to a small value that cannot be displaced by oil, and is referred to as irreducible water saturation. For practical purposes it is assumed that oil or hydrocarbon saturation of the formation is equal to one minus the water saturation. Obviously, if the formation's pore space is completely filled with water, such a formation will not produce oil or gas and is of no interest. Conversely, if the formation is at an irreducible water saturation, it will produce all hydrocarbons and no water. Finally, the permeability of a formation is a measure of the ease with which fluids can flow through the formation, i.e., it's producibility.

Traditional methods of determining these parameters called for the use of wireline logging or logging while drilling (LWD) techniques which generally include resistivity, gamma, and neutron-density measurements, commonly known as the "triple-combo." In the instance of a wireline measurement, the tool is typically lowered below the zone of interest on an armored multiconductor cable, providing for power and communications, and moved upwardly through the borehole while making the measurements. In the instance of LWD logging, the measurements are made while drilling is taking place, the tools being mounted on specialized subs in the drilling string. Each of these methods has their advantages. The wireline method is generally capable of providing a more accurate measurement as well as more real time data. The LWD method, while being more susceptible to environmental effects, such as tool position within the borehole, makes the measurements in a relatively new borehole, generally prior to any invasion by components of the drilling fluids into the formation. The triple combo measurements are subject to a number of borehole environmental effects. Resistivity tools respond to conductive fluids, including moveable water, clay bound water, capillary bound water and irreducible water. While a number of models have been developed to estimate the water saturation of the formation, the recognition of pay zones within an earth formation is difficult because no conductivity contrast exists between capillary-bound water and moveable water. Further, the resistivity measurement is subject to borehole rugosity and mudcake effects. Similarly, the methods utilized to determine porosity were lacking in detail in that neutron-density measurements responded to all components within the formation but are more sensitive to the formation matrix as opposed to the fluids contained therein. Even after cross plot corrections, borehole rugosity, mudcake, lithology and other environmental effects can adversely effect this measurement.

Nuclear magnetic resonance (NMR) logging is relatively recent commercial method developed to determine the above formation parameters, as well as other parameters of interest, for a geological formation and clearly has the potential to become the measurement of choice for characterizing formation fluids. This is due, at least in part, to the fact that unlike nuclear porosity logs, which utilize isotopic radioactive sources, the NMR measurement is environmentally safe and is less affected by variations in matrix lithology than most other logging tools. The NMR logging method is based on the observation that when an assembly of magnetic moments, each of which having a certain angular momentum, are exposed to a static magnetic field they tend to align at a certain angle to the direction of the magnetic field, and will precess with the Larmor frequency around the direction of the magnetic field. The rate at which equilibrium is established upon provision of a static magnetic field is characterized by the parameter $T_1$, known as the spin-lattice relaxation time. Another related and frequently used NMR parameter is the spin-spin relaxation time constant $T_2$ (also known as transverse relaxation time) which is an expression of the relaxation due to dynamic non-homogeneities on molecular length scales. Another measurement parameter used in NMR well logging is the self-diffusion coefficient of formation fluids, D. Generally, self-diffusion refers to the random motion of atoms in a gaseous or liquid state due to their thermal energy. Since the molecular propagation of pore fluid molecules is affected by pore geometry, the diffusion parameter D offers much promise as a separate permeability indicator. Diffusion causes atoms to move from their original positions to new ones. In a uniform magnetic field, diffusion has no effect on the decay rate of the measure to NMR echoes. In a gradient magnetic field, however, atoms that have diffused will acquire different phase shifts compared to atoms that do not move, and diffusion will thus contribute to a faster rate of relaxation.

Recent advances in the NMR logging tool design and interpretation have permitted users to obtain detailed information regarding formation characteristics porosity, fluid characterization and estimates of permeability. In particular, the MRIL® tool manufactured and utilized by the NUMAR product service line of Halliburton Energy Services and the CMR™ tool manufactured and utilized by Schlumberger Oilfield Services represent significant improvements in the field of NMR logging and are both capable of making porosity, permeability and fluid characterization measurements. Both tools utilize permanent magnets to provide a static magnetic B field and RF pulses to create a $B_1$ fields as part of Carr-Purcell-Meiboom-Gill (CPMG) experiment. Using $T_1$ and/or $T_2$ echo information, one can determine a number of formation properties. Fluid saturation (porosity) is generally determined by means of signal intensity. Fluid typing utilizes $T_1$, $T_2$ and/or diffusion measurements and is usually based on the viscosity of the fluid being measured. The bulk volume index (BVI) and free fluid index (FFI) are measured based on $T_2$ and empirically derived formulas. The formation permeability is also based on $T_1$ and/or $T_2$ measurements and one of several empirically derived models.

With respect to permeability, several models have been used to estimate formation permeability. The first method is based on $T_1$ and/or $T_2$ porosity and is estimated by various oilfield service and oil exploration companies according to equations 1–3 below:

$$k \sim \phi^4 T_1^2 \quad [1]$$

$$k = C\phi^4 T_{2ML}^2 \quad [2]$$

$$k \sim \phi^2 T_1^2 \quad [3]$$

Where k is permeability, $\phi$ is porosity, C is an empirically derived constant and $T_{2ML}$ is the logarithmic mean of the $T_2$ distribution.

Yet another model estimates formation permeability based on the bound water information (often referred to as the Coates model) according to equation 4 below:

$$k \sim \left[\left(\frac{\phi}{C}\right)^2 \left(\frac{FFI}{BVI}\right)\right]^2 \quad [4]$$

where FFI is the free fluid index, which is determined by partitioning the total measured NMR response by the $T_{2cutoff}$, which is the value of $T_2$ that is empirically related to the capillary properties of the wetting fluid for the specific formation lithology. The porosity estimate below $T_{2cutoff}$ is generally referred to as the bound fluid porosity or bulk volume irreducible (BVI). While estimates of $T_{2cutoff}$ values have been made for various types of mineralogy, the only accurate means of determining $T_{2cutoff}$ is by performing NMR measurements on a core sample.

Another model for estimating formation permeability is based on the restricted diffusion and pore size of the formation as set forth in equation 5 below:

$$k \sim \phi^3 / ((1-\phi)^2 \tau (S/V)^2) \quad [5]$$

where S/V is the pore surface to volume ratio and $\tau$ is the rock tortuosity.

Each of the above models has drawbacks in their application. For instance, equation 4 (the Coates model) might not be valid if gas is present in the sample or if the estimate of the $T_{2cutoff}$ is significantly in error. The Carman-Kozeny model set forth in equation 5 was derived for an artificial lithology (glass beads) and has yet to be verified over wide range of reservoir lithology.

Other techniques have been used to estimate formation permeability. Primary among them is the use of formation test tools to determine formation permeability. A formation test tool is generally lowered into the borehole and brought into contact with the formation wall. A probe is inserted past the mud cake to come in contact with the formation itself. Fluid is then withdrawn from the formation using a pre-charge piston or pumping means. This "draw down" period induces fluid into the tool that may be diverted to sampling chambers or, ultimately, discharged back into the borehole. Following the draw down, formation pressure (and generally temperature) is measured as it builds back up to its natural formation pressure. There are a number of models for estimating permeability based on the formation pressure and temperature tool data. These models may include a laminar or spherical model design. The use of formation testers to determine permeability is well known and U.S. Pat. Nos. 6,047,239, 5,2447,830 and 4,745,802 set forth exemplary formation test tools. As noted previously, these formation test evaluation techniques pre-suppose the use of a particular model, which in turn pre-supposes the nature of the formation itself. The formation may be thinly laminated near the test point or have a large, consistent lithology. It will be appreciated that models designed to work in a consistent lithology will not yield as accurate a result where the formation is thinly laminated with the layers each having differing porosity and permeability characteristics. Formation test tools are generally incapable of measuring anisotropic permeability, i.e., vertical versus horizontal permeability. An additional downside to using formation test tools is the fact that logging tool movement must be stopped to permit the formation test tool to come into contact with formation, perform the draw down and permit the pressure to build back up. It may require several minutes to hours to perform the draw down and build up. It will be further appreciated prior to wireline logging operations, the drill string must be "tripped" or removed from the borehole to permit logging. This results in an associated cost over and beyond the cost of services associated with logging. The triple-combo and NMR logging tools noted above are used in continuous logging operations, that is, the measurements are made as the tool is moved up or down the borehole at rates exceeding three feet per minute. Indeed, modern borehole logging speeds generally exceed 30 feet per minute. Thus, while providing some information regarding permeability, formation test tools are costly to use when compared to NMR logging tools. At the same time, NMR logging tools make certain assumptions regarding permeability that may not be accurate in light of actual formation conditions.

Recently, some efforts have been made to combine NMR techniques with formation test tools. Halliburton, Schlumberger and Baker Atlas have introduced techniques in which fluid identification is performed on the fluid withdrawn from the formation during one of the formation tests. Examples on these types of techniques are set forth in U.S. Pat. Nos. 6,111,408 and 6,111,409. In each instance, the NMR experiment is performed on the fluid that is no longer in situ. As a result, it may undergo a phase change.

Other methods of formation characterization include in the use of imaging tools. These tools attempt to create an image of the borehole wall as it surrounds the tool. There are a number of different techniques utilized in this area. Primary among them are the use of acoustic or sonic information and microresistivity. Borehole acoustic imaging tools typically utilize an ultrasonic transducer to emit high frequency sonic energy that is reflected back from the borehole. The reflected signal is received by the transceiver and processed to create an image. The microresistivity technique places small electrodes against the side of the borehole wall and current is forced into the formation. Based on the return resistivity information, an image of the borehole wall can likewise be created. Both of these techniques have their drawbacks in that both require a great amount of time to hold the tools stationary in the borehole in order to make measurements. In the case of the electrical technique, the electrodes must be in contact with the borehole wall. Further, commonly used oil-based drilling muds have an adverse effect on the use of the microresistivity method. It will be appreciated that both of these techniques significantly increase the amount of time required for logging operations. Moreover, they provide only a portion of the information that may be sought in order to characterize the reservoir.

Further, there exists a continued need for accurately determining formation permeability at present, formation permeability can be derived in a number of different ways. One method utilizes a formation test tool wherein a small section of the borehole wall is isolated from the borehole. A fluid channel between the formation and the tool is created and fluid is drawn into the tool over a period of time. Pressure, temperature and fluid volumes are recorded and permeability is empirically derived using various models. Permeability may also be empirically derived utilizing NMR tools based on fluid volumes and various models.

Thus, there exits a need for a means for directly determining formation permeability, as well as providing an image of the formation where the measurement is made. Further, there exists a need for a means for determining anisotropic permeability where vertical permeability ($k_V$) differs from horizontal permeability ($k_H$).

SUMMARY OF THE PRESENT INVENTION

The present invention is directed to a means for measuring formation characteristics, including determining formation porosity, permeability, fluid characterization and imaging of the well borehole. It relates more particularly to a method and apparatus for measuring a property relating to fluid flow in an earth formation, more specifically to directly measuring formation permeability.

In one embodiment, the present invention utilizes one or more small NMR imaging sensors in conjunction with a formation test tool, the sensors being in or proximate to the borehole wall during the formation test procedures. The present invention is thus capable of performing fluid typing of the fluid in situ as it flows toward the formation test tool probe. This permits a determination of actual flow velocity of connate fluids within the formation based on the displacement of the hydrogen atoms within the formation. It is, thus, further an objective of the present invention to provide for a more accurate determination of permeability, including anisotropic permeability measured in situ.

The apparatus of the present invention further is capable of creating a 3 dimensional image of the borehole. Unlike prior part techniques, which utilize Free Induction Decay (FID) CPMG experiments and/or Saturation Recovery techniques, the present invention is capable of utilizing a Pulsed Field Gradient (PFG) pulse sequence to measure single point echo information to derive spin density for a myriad of "voxel" or scan positions at the borehole wall and into the formation. Voxel is a commonly used term to denote a volume picture element, which is used as smallest division of a three-dimensional space or image. This spin density information is used to create an image of the formation at depths exceeding that of near surface images. In one embodiment, the apparatus of the present invention utilizes a series of permanent magnets and electromagnets to create a static magnetic field and a pulsed magnetic field to perform the PFG experiment. The electromagnets are under independent programmable control and may be used to control the magnetic field at each of the voxel positions. This control feature may be used to create a 3-D grid of voxels, thereby providing a 3-D image of the formation surrounding borehole wall.

In another alternative embodiment, this present invention may be utilized in conjunction with a formation test tool to create an image of the formation fluid flowing into the test tool to determine fluid characteristics, including self-diffusion.

In yet another alternative embodiment, the present invention provides for utilizing existing NMR tool structures and designs modified to include electromagnetic coils in addition to permanent magnets. In this embodiment, the present invention may be utilized with a separate formation test tool, or may be run on a stand-alone basis and derive permeability from known models. The addition of electromagnetic coils permit carrying out the PFG experiment for the purpose of imaging, as well as any CPMG experiments to determine other formation characteristics such as porosity, permeability (using existing models), and fluid typing.

In yet another alternative embodiment, the present invention provides for a centralized NMR apparatus including both permanent and electromagnets to create an azimuthal image of the borehole wall. In this particular embodiment, the tool is not measuring flow formation and known techniques for estimating permeability based on NMR data may be used. At the same time, the embodiment includes a combination of permanent magnets and independently controllable electromagnets to create voxels in the sensitive volume and carry out the necessary PFG experiments to provide a 3D image of the borehole. As with the embodiment noted above, this embodiment is capable of utilizing existing CPMG techniques to determine porosity, permeability and fluid characterization.

The present invention thus provides the user the ability to accurately determine formation parameters as well as obtain a 3-D image of the formation past the borehole wall. This image information can be used in conjunction with other logging information to provide the user with the information required to make decisions regarding the completion and production of wells.

BRIEF DESCRIPTION OF THE DRAWINGS

A better understanding of the present invention may be had by reference to the detailed description of the preferred embodiment and the Figures referenced therein in which:

FIGS. 24A and 24B are depictions of the "thirteen interval" sequence that may be used to suppress background gradient information;

FIGS. 25A and 25B is a depiction of sequences utilizing bipolar pulsed field gradients to encode and obtain information related to POSXY and VEXSY experiments to determine fluid displacement, velocity and acceleration.

DETAILED DESCRIPTION PREFERRED EMBODIMENT

Figure 1:
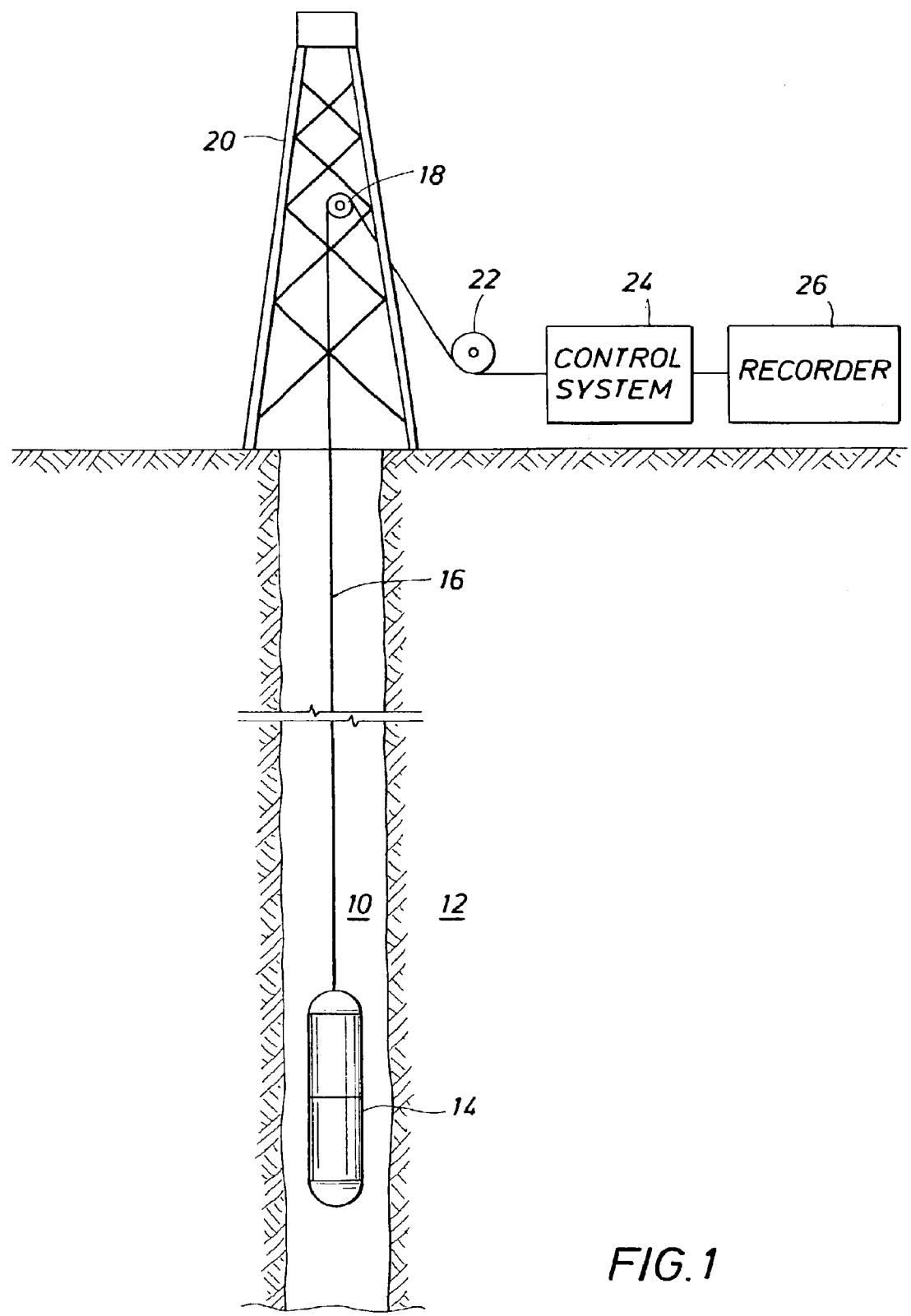
FIG. 1 is an illustration of a logging system.

The present invention is intended to be used as an NMR imaging device within a well borehole. Use of the present invention within the well borehole is intended to provide certain formation characteristics, including, porosity, permeability, fluid characterization, flow velocity and 3-D imaging of the formation of interest. With reference to FIG. 1, a well logging system is generally depicted. A well borehole 10 is seen as penetrating earth formation 12, having been drilled using known methods. A well logging tool 14 is seen as being lowered into the well borehole and on an armored, multiconductor cable 16. The tool 14 includes the sensors required for the measurement(s) to be made, power conditioning circuitry, tool control processors, and telemetry circuitry to transmit the information back up the cable 16. The cable 16 is lowered over shiv wheel 18, which is in turn supported by rig 20. The cable 16 is played out from a winch 22, controlled by an operator within a well logging truck or skid (not shown). The cable 16 includes conductors that provide for power, control signals to and control and data information from the tool 14. The conductors are thus connected to a control system 24, which is generally includes a processor for tool programming and operation, as well as data reception and interpretation. The tool data, as well as interpretations created, may be stored in recorder 26 that may be disk, tape or other mass storage system located at the logging site. Further, the information may be visually displayed on a monitor, CRT, log chart, or other visual means of display (not shown). In addition or in the alternative, the tool data and interpretation information may be communicated via satellite or land lines (not shown) to a remote location for further interpretation by persons having specialized knowledge relevant to logging information or formation characterization, including other interpretation software or visualization software. The tool 14 is shown as being a single tool being lowered on a wireline. It will be appreciated that in practice, multiple tools may be lowered on the wireline for a single run. The number of tools that may be included in any single run can be limited by a number of factors, including compatibility, power consumption, and telemetry requirements.

Figure 2:
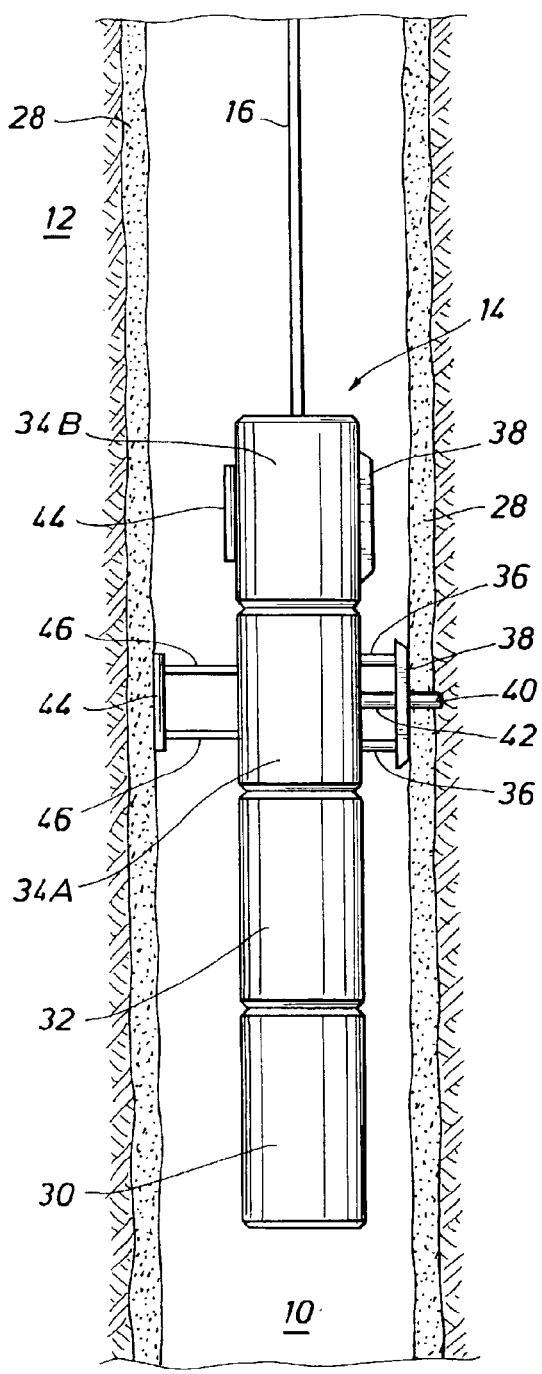
FIG. 2 is an illustration of a formation test tool deployed in a well borehole.

FIG. 2 depicts tool 14 as being a modular formation test tool. As noted above, the tool 14 is lowered on armored cable 16 to the zone of interest. In the instance of a formation test tool, the tool 14 is stationary when it makes its measurements. The borehole 10 is generally filled with a mud or other weighted fluid used to control wellbore pressure. The mud also operates to seal and support the borehole by forming a mud cake 28 on the borehole wall. The mud cake 28 also reduces invasion of formation fluids into the borehole 10. The formation test tool 14 of FIG. 2 is shown as being comprised of several modules, 30, 32, 34A and 34B. Recent developments in formation tester design have resulted in "modular" testers that permit the user to configure the tool 14 for the specific application. It might include one or more control and power section 30, a module for multiple sample chambers 32, and, as depicted in FIG. 2, two sample modules 34A and 34B. Tools of this type include Schlumberger's MDT, Halliburton's RDT and Baker Atlas' RCI formation test tools. Typically, the tool 14 is eccentered in the borehole by the extension of eccentering arms 46 that bring pad 44 in contact with the borehole wall opposite the formation tool tester. The eccentering arms 46 are typically hydraulically actuated. As the tool 14 is eccentered in the borehole 10, the sampling apparatus is extended. The apparatus typically consists of hydraulically actuated extension arms 36 that push a typically elastomeric isolation pad 38 into contact with mud cake 28. A probe or snorkel 40 is mounted in the center of the pad and is extended once pad 38 comes into contact with the mud cake 28 to position snorkel 40 proximate to the formation 12. The pad 38 is used to isolate probe 40 from borehole fluids that may adversely affect any pressure readings and/or fluid characterization. A number of techniques have been developed to isolate the snorkel 40 from the borehole fluids and any influx of mud from the mud cake 28. The snorkel 40 is in fluid communications with transport tube 42, which is itself in fluid communication with the pre-test piston or pump (not shown), and/or fluid sampling chambers located in module 32. Temperature and pressure sensors are located in sample modules 34A. Additional sensors for fluid characterization, e.g., NMR spectroscopy units, acoustic sensors, or optical sensors may be located in any of the modules. Module 34B depicts the snorkel 40, isolation pad 38 and eccentering pad 44 in the withdrawn position to permit transit up or down the borehole 10. The tool 14 is typically lowered to the desired test depth with the sampling mechanism in the position depicted in module 34B. The eccentering pad 44 and isolation pad 38 systems are actuated to move the tool 10 into position against the borehole 10 wall. The snorkel 40 is then actuated to extend toward the formation 12 and the programmed test program is carried out. It will be appreciated that the test program will vary with the parameters to be measured, the nature of the formation 12 and the number of samples (if any to be taken). The tool sampling apparatus is then deactivated and the eccentering pad 44 and isolation pad 38 return to the positions shown in module 34B. The tool 14 may then be moved to a different depth for additional testing or returned to the surface.

Permeability maybe derived from the formation tester pressure and temperature according to several well-known models. One model utilizes a spherical flow model to approximate fluid flow from the formation into the snorkel 40. This technique is described in U.S. Pat. No. 5,703,286. Other models postulate that the fluid flow to the snorkel 40 takes place in the form of a generally laminar flow model. This technique is described in U.S. Pat. No. 4,427,944. There exist other techniques for the determination of fluid permeability directed to specific applications, e.g., tight (very low) porosity measurements, multiphase techniques, etc. These techniques may be applied in addition to the method and apparatus described in further detail below.

Structural Embodiments for Carrying Out the Method of the Present Invention

Figure 3A:
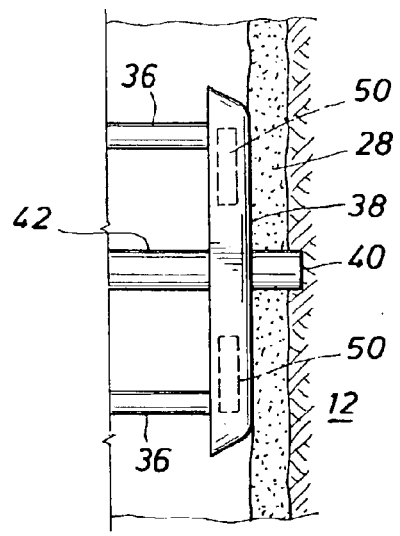
FIGS. 3A and 3B are illustrations of a formation test tool utilizing NMR spectroscopy sensors.
Figure 3B:
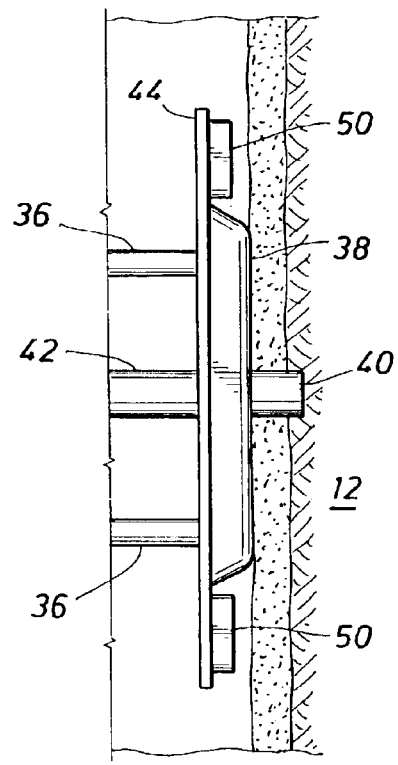

FIGS. 3A and 3B illustrate one embodiment of the present invention in which the NMR imaging sensors 50 (described in greater detail below) are used in conjunction with a formation test tool. In FIG. 3A, two NMR sensors 50 are depicted as being placed within the isolation pad 38. As the isolation pad 38 is advanced toward to formation 12, the sensors likewise come into close proximity with the formation 12. As will be set forth further below, the NMR sensor 50 of this embodiment is intended to operate in close proximity to the borehole 10 wall. In FIG. 3B, the NMR sensors 50 are mounted adjoining isolation pad 38 as opposed to within the pad 38 itself.

Figure 4A:
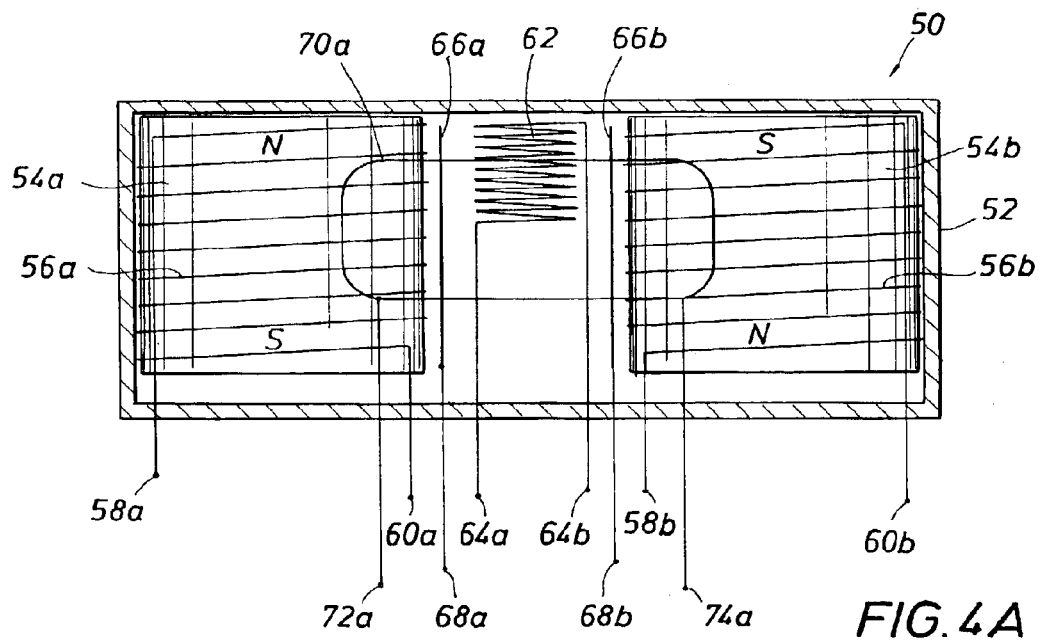
FIGS. 4A and 4B are illustrations of embodiments of the NMR spectroscopy magnet and antenna configuration of the present invention.

The NMR sensor 50 embedded used in conjunction with a formation tester as shown in FIGS. 3A and 3B does not represent the entire NMR imaging apparatus. The NMR sensor 50 referred to is limited to the permanent magnet, electromagnet and RF transmit/receive antenna design. The electronics and power section for the operation of the tool of the present invention would reside in the tool body 14 and within the surface system 24. One embodiment of the NMR sensor capable of performing known NMR, Pulsed Field Gradient (PFG) NMR, and MRI imaging experiments is depicted in FIG. 4A, which is a top view of the NMR sensor 50. The sensor is encased in a protective package 52 designed to protect the sensor antenna and magnet structure from ambient conditions, including fluids, pressure and shock. Two permanent magnets 54a and 54b are being disposed in the sensor 50, the axes of the magnets 54a and 54b (between the poles for each respective magnet) being coplanar. The magnets 54a and 54b are oriented such that the North pole of magnet 54a is adjacent to the South pole of magnet 54b. The permanent magnets 54a and 54b are used to form the $B_0$ field for the NMR experiments to be carried out with the present invention. Each of the permanent magnets 54a and 54b has a coil 56a and 56b wound about the magnet. Coil 56a has leads 58a and 60a to provide power to the coil to create an electromagnet (EM coil) when powered. Likewise, coil 56b has leads 58b and 60b to provide power to the coil to create an electromagnet. The EM coils 56a and 56b may be independently energized and are used to provide the $G_s$ (slice selection) magnetic field gradient utilized in one embodiment of the present invention. A radio frequency (RF) coil 62, having leads 64a and 64b is shown as being disposed between magnets 54a and 54b, The radio frequency coil 62 is designed such that its magnetic field is oriented orthogonal to the direction of the effective magnetic field created by the permanent magnets 54a and 54b and coils 56a and 56b. Two EM coils 66a and 66b, having leads 68a, 69a(not shown) and 68b, 69b(not shown), respectively are shown as being disposed between magnets 54a and 54b. The coils 66a and 66b may be comprised of multiple winding or may consist of a single EM coil, the coil(s) lying in a plane that is parallel to the axes of magnets 54a and 54b and substantially orthogonal to the plane of the coils of the RF antenna 62. The EM coils 66a and 66b may be independently energized and are used to provide the $G_\phi$ (phase encoding) magnet gradient field. They may also be used to provide frequency encoding along depth by the time invariant gradient. Yet another EM coil 70a having leads 72a and 74a is shown in FIG. 4A. Not shown is a corresponding coil 70b, having leads 72b and 74b, which is disposed below the magnets 54a and 54b and is similarly positioned. The coils 70a and 70b may be independently energized and are used to provide the $G_f$ (frequency encoding) magnet field gradient utilized in the present embodiment. EM coils 56a and 56b are shown as being wound about magnets 54a and 54b. It will be appreciated that EM coils 56a and 56b may instead be wound about ferrite cores disposed in parallel to magnets 54a and 54b to provide the $G_s$ magnetic field gradient. The magnet/antenna structure set forth in FIG. 4A is capable of performing known CPMG experiments to determine various formation characteristics, including porosity, permeability, and fluid typing.

Figure 4B:
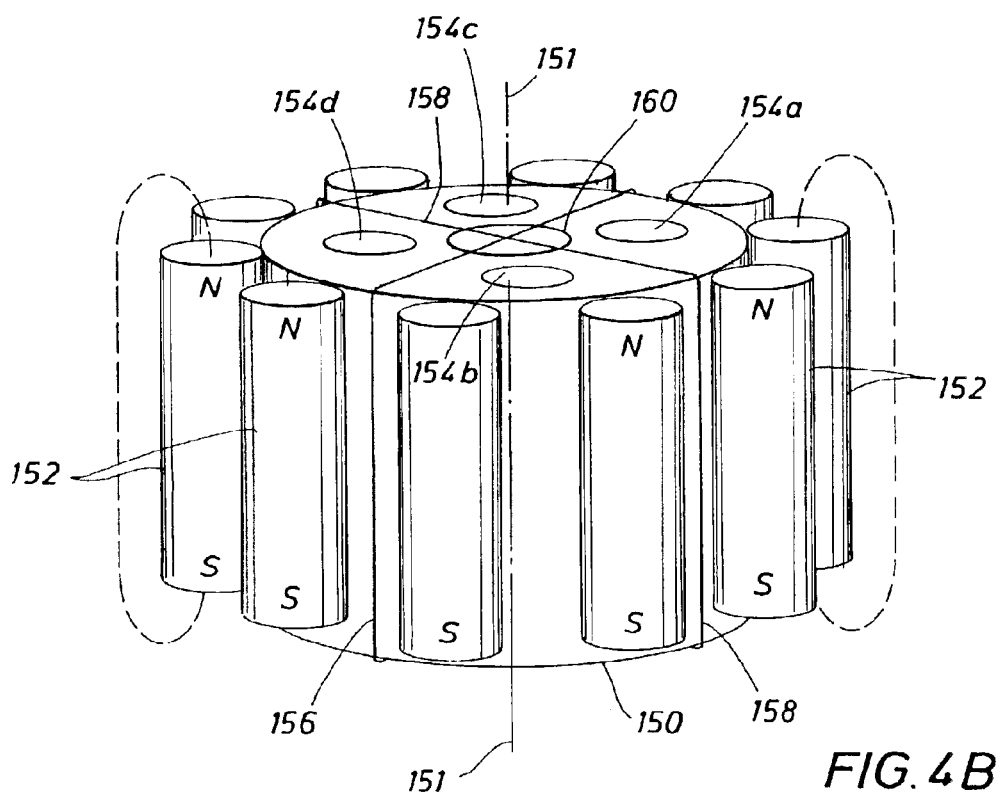
Figure 5:
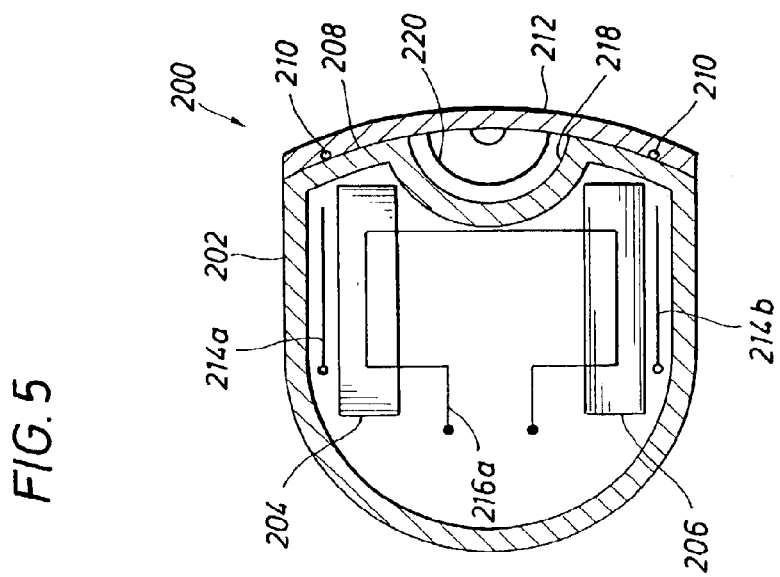
FIG. 5 is an illustration of a known NMR apparatus modified to provide the functionality of the present invention.

An alternative embodiment of NMR sensor 50 is shown in FIG. 4B The sensor is comprised of a non-magnetic body 150, having an axis 151. A plurality of bar magnets 152 are circumferentially deployed about body 150, having a common polarity orientation, the axes of the bar magnets 152 being parallel to the axis 151 of body 152. The bar magnets provide the static $B_0$ field. Four electromagnets, 154a, 154b, 154c and 154d, are embedded in the body 152 and may be energized as explained in the discussion of FIG. 7. These magnets provide one orthogonal component to the gradient field. An electromagnetic coil 156 is wrapped around the body 150 and when energized creates a magnetic vector essentially perpendicular to the axis of body 150 and bar magnets 152. A second electromagnetic coil 158 is wrapped around body 152 and when energized, creates a magnetic vector that is orthogonal to the $B_0$ vector and the magnetic vector created by coil 156. Lastly, a RF coil 160 is mounted on the face of the body to provide for the $B_1$ field. Thus, the bar magnets 152 create a static $B_0$ field, the electromagnets 154a–d, 156 and 158 may be used to create a selective gradient field and coil 160 may be used for RF pulses to carry out the NMR and MRI activities within the present invention. While the embodiments set forth in FIGS. 4A and 4B describe concentrically wound coils or individual magnets, FIG. 5 is an illustration of a modification of a known NMR apparatus to provide the functionality of the present invention, in particular the imaging capability. The NMR logging that may be modified in accordance with the present invention is disclosed in U.S. Pat. No. 5,796,252 and is a variant of Schlumberger's CMR tool. While the apparatus disclosed therein is capable of performing both PFG and CPMG experiments, it is incapable of addressing individual voxels with the pulsed magnetic field for the purposes of imaging. FIG. 5 is an sectional view of a CMR tool, which has been modified to perform various CPMG experiments as are known in the art of oilfield logging, as well as the PFG imaging experiments of the present invention as well.

In FIG. 5, the CMR tool 200 modified to provide the functionality of the present invention is generally described. The tool 200 is comprised of a tool body 202 having magnets 204 and 206 disposed therein. In FIG. 5, magnets 204 and 206 appear to be bar magnets. In fact, they are slab magnets, having a longitudinal axes, one pole of the magnet being located on one edge of the slab and the opposite pole of the magnet on the opposite edge of the slab. The magnetization directions of both magnets 204 and 206 are perpendicular to the axes of the magnets. The tool body 202 further includes a cavity 218 in which is disposed a RF antenna 220 having a semi-circular cross section. An EM coil 210 is shown as being disposed on the face 208 of the tool body 202. The EM coil 210 is energized to provide the $G_s$ gradient magnetic field within the present invention. The embodiment further includes EM coils 214a and 214b, each of which may be independently energized, to provide the $G_\phi$ gradient magnetic field in the present invention. The coil(s) of EM coils 214a and 214b lie in a plane that is substantially parallel to the magnetization direction of magnets 204 and 206. Lastly, two independently energizable EM coils 216a and 216b (not shown) are shown as being disposed in a plane that is orthogonal to the magnets 204 and 206 longitudinal axes and substantially parallel to the magnetization direction of magnets 204 and 206. It will be appreciated that EM coil 216b is located beneath bar magnets 204 and 206. EM coils 216a and 216b are energized to provide the $G_f$ magnetic field gradient utilized in the present invention as further described below. The embodiment of FIG. 5, while illustrated in the context of an eccentered self-standing probe could be combined with a formation test tool as shown in FIGS. 3A and 3B or continue to be used on a stand-alone basis. Where used as a self standing tool, it can derive permeability of the formation utilizing the models described above. Moreover, it may be used in conjunction with a formation test tool to provide additional information.

Figure 6:
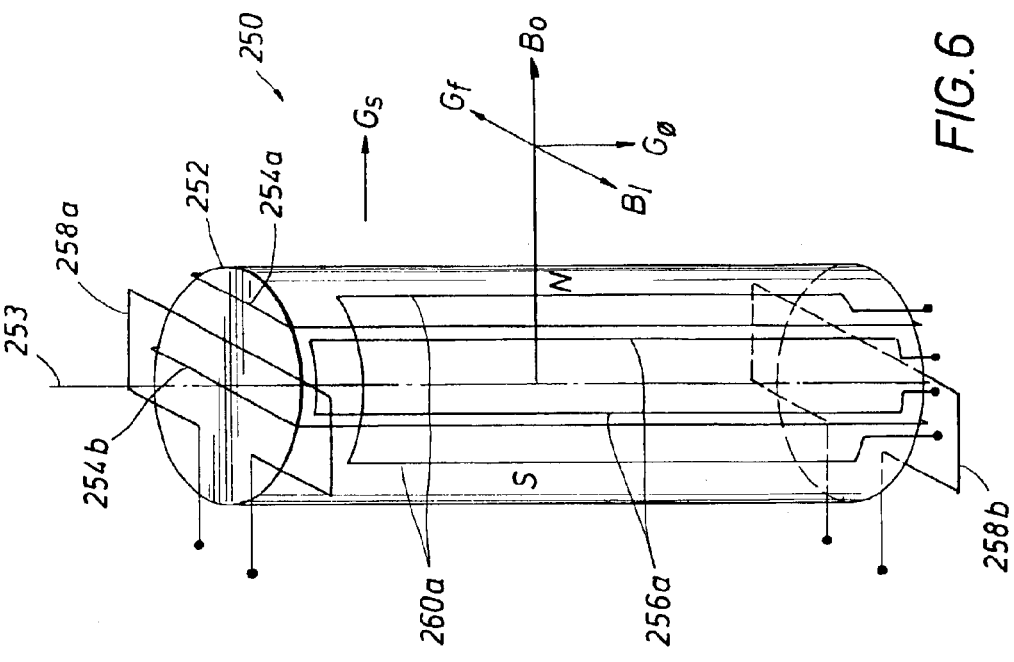
FIG. 6 is an illustration of yet another known NMR apparatus modified to provide the functionality of the present invention.

FIG. 6 is another embodiment, which modifies an existing NMR device to perform the intended CPMG experiments, as well as the PFG MRI imaging of the present invention. U.S. Pat. No. 4,710,713 (FIGS. 1 and 2) describes the magnet and antenna structure that is utilized in the Halliburton/NUMAR MRIL tool. Unlike the CMR tool, which is eccentered and located adjacent to the borehole wall during operation, the MRIL tool is a centralized design. Thus, the magnet and RF antennae structures are not located against the borehole wall. While it will be appreciated that improvements may have been made to the antenna and magnet design, it remains the basic structure. A variation of the MRIL tool that added electromagnets to the $B_0$ field activation is disclosed in U.S. Pat. No. 4,717,877 (FIGS. 1 and 2), also assigned to Halliburton/NUMAR. The modifications to the magnet and antenna structure of U.S. Pat. No. 4,717,877 are set forth in FIG. 6. FIG. 6 is an oblique view of the modified MRIL tool 250 in keeping with the present invention. A permanent magnet 252 is shown having a magnetization direction that is essentially perpendicular to the magnet 252 longitudinal axis 253. The permanent magnet 252 is used to create the $B_0$ field. The embodiment further includes EM coils 254a and 254b, which may be independently energized to create the $G_s$ magnetic field gradient. As depicted in FIG. 6, EM coils 254a and 254b are wound about magnet 252, such that the coils lie in a plane substantially orthogonal to the magnetization direction of magnet 252. The structure further includes RF antennae 256a and 256b (not shown) disposed along the side of magnet 252 used to propagate the RF pulse to create the $B_1$ field for the MRIL tool. Additional EM coils 258a and 258b are shown as being generally disposed above and below magnet 252 and may be energized independent of each other. EM coils 258a and 258b, when energized, are used to provide the $G_\phi$ magnetic field gradient used within the present invention. Lastly, EM coils 260a and 260b (not shown) are disposed about permanent magnet 252, in a manner similar to the RF antennae 256a and 256b. EM coils 260a and 260b may be independently energized and, when energized, provide the $G_f$ magnetic field gradient of the present invention. It should be further noted that the recent MRIL-Prime version of this tool is capable of performing multi-frequency NMR experiments. See, e.g., U.S. Pat. Nos. 5,936,405 and 6,111,408. Utilizing the multiple frequencies, multiple sensitive volumes at varying radial distances may be investigated utilizing a single $B_0$ field. Accordingly, it will be appreciated that the volumes for imaging may likewise be extended further into the formation.

As depicted in FIG. 6, the MRI apparatus of the present invention is capable of providing and image for the formation past the borehole wall in a specific volume only where the resultant $B_0$, $B_1$, $G_s$, $G_\phi$ and $G_f$ fields are operative to permit imaging. It does not provide an azimuthally resolved picture of the formation. The present invention further contemplates providing azimuthally resolved images of the formation. One means of providing an azimuthally resolved image is similar to the technique utilized in microresistivity imaging, using tools such as Schlumberger's FRI™, Halliburton's EMI™ and Baker Atlas' STAR™ tools. Typically, a multi-arm dipmeter, well known in the art, includes multiple microresistivity buttons or electrodes on each dipmeter pad to provide a derived image of the borehole wall. The dipmeter provides information as to the relative position of the arms, the tool within the borehole and the formation inclination or dip. Thus, an image of the borehole wall is generated from the resistivity information. In an azimuthally resolved imaging embodiment of the present invention, NMR sensors of the type disclosed in FIG. 4 may likewise be mounted on the dipmeter arm pads to provide known NMR formation characterization information as well as imaging information which may be resolved to provide an azimuthally resolved image of the formation past the borehole wall.

Another means of providing an azimuthally resolved image would be to rotate the structure set forth in FIG. 6. This may be accomplished in a wireline environment by providing a rotating tool head, such that the magnet/antenna structure is free to rotate with respect to the tool electronics and the remainder of the wireline tool string. Such a system would further require an orientation package to correlate NMR imaging data with the tool azimuth and position. Known techniques utilizing 3-axis accelerometers, gyroscopes, magnetometers or other directional sensing equipment may be used to correlate the imaging data with the tool position in the borehole, including tool azimuth (face). Another alternative means of providing an azimuthally resolved NMR image would be to mount the structure of FIG. 6 as part of a LWD logging string sub. The structure would be positioned where logging information is desired and the drill string rotated to provide azimuthal resolution. While a drill string undergoes torque displacement over its length, the navigation package typically utilized in LWD apparatus includes magnetometers, accelerometers and other known sensors to establish the position of the tool face.

By establishing the tool face and the position of the NMR tool relative to the tool face, one can establish azimuth during the logging position to obtain azimuthally resolved NMR images. While NMR logging is typically a continuous operation, the use of tools to provide MRI information will require a cessation of tool movement for the time required to form the image. As discussed below, the faster the image can be obtained, the less time required for logging operations.

Figure 7:
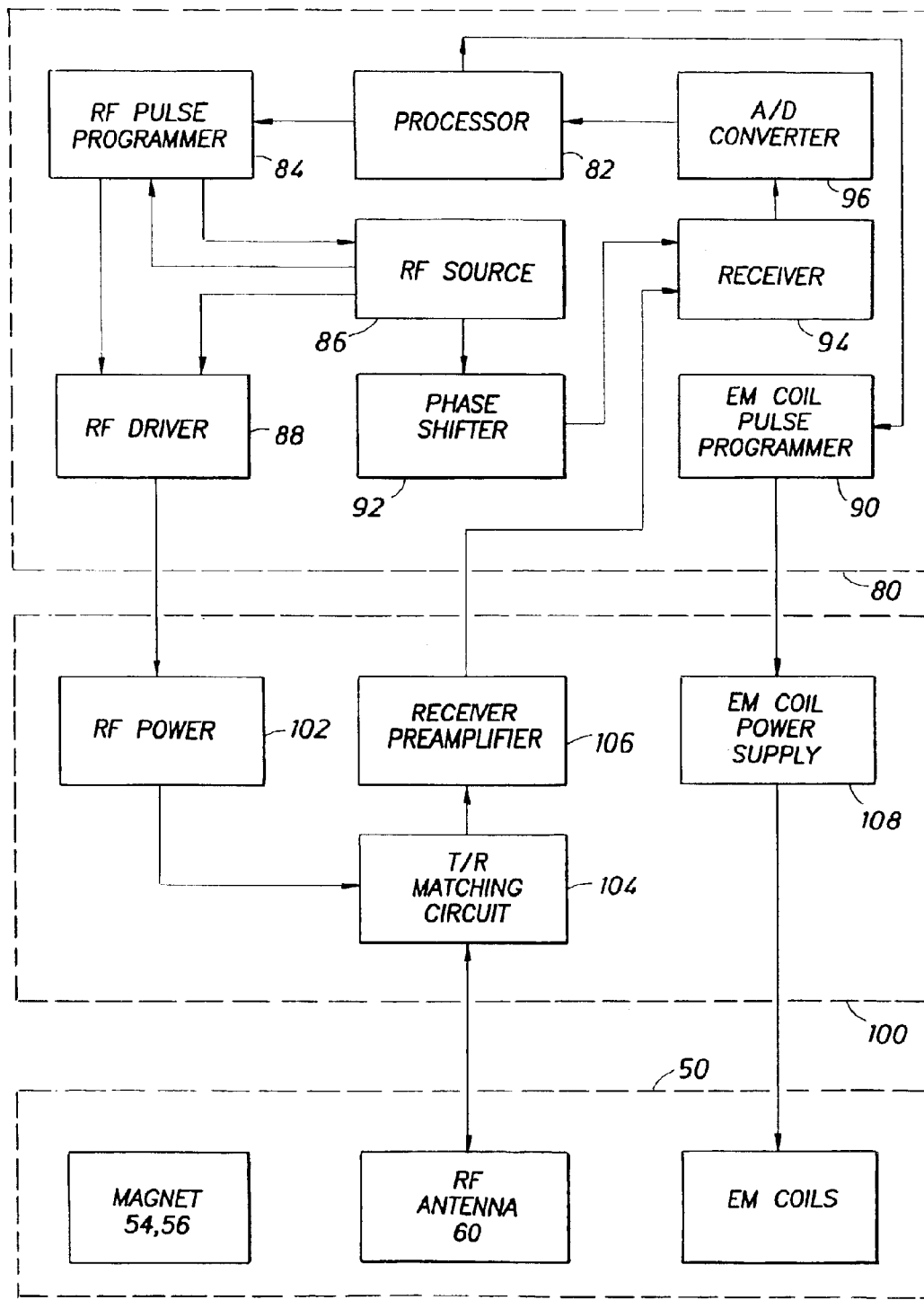
FIG. 7 is a block diagram of the NMR control system of the present invention.

FIG. 7 is a block diagram of the system of an apparatus for carrying out the present invention and consists of the control section 80, power section 100 and MRI sensor 50. It will be appreciated that the control 80 and power 100 sections may be located at the surface or, in the case of power section 100, within the tool 14 itself. To the extent portions of the system may be located at the surface, a telemetry system (not shown) is utilized to transfer control and data between elements located in the borehole 10 is incorporated in the tool 14 and control system 24. The control section includes processor 82 that is utilized for overall signal processing, tool control and RF and electromagnetic control. The user may program the processor 82 to specify various pulse sequences. The processor 82 is in communications with an RF pulse programmer 84 used to create the RF pulse sequence utilized in the MRI experiment. The RF Pulse Programmer 84 signal is also provided to an RF Source 86, the output of which is provided to the RF Driver 88, the Phase Shifter 92 and back to the RF Pulse Programmer 84 for verification. The RF driver 88, which, together with input from the RF Source 86 is utilized to create the signal that is applied to the RF power supply 102, within the power section 100 of the system. The RF signal is communicated to the Transmit/Receive matching circuit 104. The signal is then communicated to the RF Antenna 60 within MRI sensor 50.

The processor 82 is also used to provide programming information for the electromagnet system. The processor 82 is in signal communications with the EM Coil Pulse Programmer 90. The signal output for the electromagnetic coils is provided to the EM Coil Power supply 108 within the Power section 100. The output from the EM Coil Power supply is then applied to the EM Coils within the MRI sensor 50. It will be appreciated that the power supplied to the EM coils would be applicable to any of the above embodiments described above.

Following the programmed pulse sequence, the Transmit/Receive Matching circuit 104 goes into a receive mode, and is in signal communications with the RF Antenna 60. The RF Antenna 60 receives the spin-echo(s) resulting from the NMR experiment and receives the spin-echo as an analog signal that is transmitted through the Transmit/Receive matching circuit 104 to the Receiver Preamplifier 106 within the power section 100. The spin-echo signal is then forwarded to the Receiver 94, together with the reference phase information provided by the Phase Shifter 92, the Receiver 94 then forwards the signal to the Analog/Digital Converter 96 which converts the signal and provides same to Processor 82 for further interpretation.

Imaging Techniques

Figure 8:
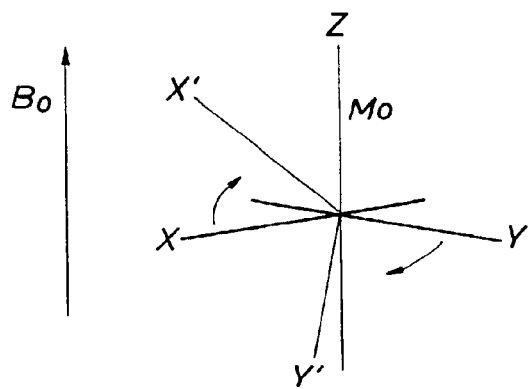
FIG. 8 is an illustration of the rotating frame of reference used in NMR/MRI techniques.

As previously noted, the use of NMR techniques in the logging of a well borehole is well known by those of ordinary skill in the art. New techniques and apparatus are continually being developed in the wireline and LWD NMR logging fields. With a few exceptions, e.g., U.S. Pat. Nos. 4,717,877 and 5,796,252, all of the tools use some variant of CPMG experiments. The aforementioned '877 and '252 patents utilize a pulsed field gradient in conjunction with a CPMG experiment. Even so, the PFG/CPMG experiments described therein are incapable of providing a MRI image. There exist a number of differing techniques that may be used to image the formation surrounding the borehole, many of them finding their genesis in the medical MRI field. In the following discussion, the spin characteristics of hydrogen nuclei are discussed in terms of a frame of reference, with X, Y and Z axes being depicted as in FIG. 8. In reality, the frame of reference is rotating about the Z axis at the Larmor frequency for the nuclei being studied—in this instance, hydrogen. The rotating frame of reference in the transverse plane is referred to herein as X' and Y' which, again, rotates at the Larmor frequency. Nuclei spinning faster than the Larmor frequency appear to precess the rotating frame of reference while those spinning slower appear to fall behind the movement of the rotating frame of reference. This difference in spin velocities results in the dephasing of the rotating nuclei.

1. Imaging Principles
   a. FID and Back Projection Techniques

The basic principles in a NMR experiment begins with the resonance equation, in which the resonance frequency of a spin is proportional to the $B_0$ magnetic field:

$$\nu = \gamma B_0 \quad [6]$$

where $\gamma$ is the gyromagnetic ratio for the nuclei being studied In the field of MRI, one employs additional linear magnetic gradient field, smaller than the $B_0$, which has the effect of modifying the Larmor frequency as a function of the combined magnetic field at the point being studied:

$$\nu(r) = \gamma B_0 + \gamma G \cdot r \quad [7]$$

where G is the gradient of the magnetic field, $B_0$, and r is the vector of the particular nuclear spin coordinates with respect to the isocenter of the $B_0$ field. Therefore, if a linear gradient field is applied to the volume of investigation, each region will experience a differing magnetic field. The amplitude of the signal is proportional to the number of spins in a plane perpendicular to the applied gradient. The thickness of this plane depends on the intensity of the field gradient and the duration of the radio frequency pulses. The discrimination of positions can be achieved by means of frequency encoding or phase encoding. The basic technique behind frequency encoding is set forth in FIG. 28a. Therein, following application of the $B_0$ field, the $B_1$ field (TX) is applied, followed by the Hahn echo (RX). The $G_y$ gradient is applied for $t_1$ followed by the application of the $G_x$ gradient for time $t_2 = n_2 \Delta t_2$. In frequency encoding, one varies $n_2$, with the resultant signal being:

$$s(n_2) = \exp(-[1/T_2 + i\gamma(B_0 + G_x x)]n_2 \Delta t_2) \quad [8]$$

where $n_2$ counts the numbers of data points along the x direction. The spatial resolution of the frequency encoding technique is limited by:

$$|\gamma G_x \Delta x| \geq 2/T_2 = \Delta \omega_{1/2} \text{ and} \quad [9A]$$

$$1/\Delta x = T_2 \gamma G_x / 2 = \gamma G_x / \Delta \omega_{1/2} \quad [9B]$$

The technique used to perform phase encoding is depicted in FIG. 28b. Therein the amplitude of the $G_y$ field is varied to step through k space. The resulting signal may be expressed as:

$$s(n_1) = \exp(-\lfloor 1/T_2 + i\gamma(B_0 + n_1 \Delta G_y y)\rfloor t_1) \quad [10]$$

where $n_1$ counts the number of data points along the y direction. In this instance, the spatial resolution increases using phase encoding with $n_{1,\,MAX}$:

$$|\gamma n_{1,MAX} \Delta G_y \Delta y t_1| < 2\pi \text{ and} \quad [11A]$$

$$1/\Delta y = n_{1,MAX} \gamma \Delta G_y t_1 / 2\pi \quad [11B]$$

The variation of the local magnetic field brought about by a field gradient pulse of intensity G and duration t adds an additional phase φ to a magnetic moment precessing at location r:

$$\phi = \gamma t G \cdot r. \quad [12]$$

MRI imaging pulse sequences are typically based on the acquisition of spin-echoes. Spin echoes occur when the dephasing of rotating magnetic moments has been compensated for by use of refocusing radio frequency pulses. Spin-echo imaging pulse sequences comprise at least two identical magnetic field gradient pulses, one of which is applied prior to, the other one after the refocusing RF pulse. It will be appreciated that these field gradient pulses can be realized using a constant field gradient and a refocusing RF pulse. In that case, the duration of the first field gradient pulse is given by the time from the beginning of the pulse sequence to the beginning of the RF pulse, and the duration of the second field gradient pulse is equal to the time from the end of the RF refocusing pulse to the peak of the spin echo.

If the magnetic moments have not changed their position r during the time between the two field gradient pulses, the second field gradient pulse will exactly compensate for the additional phase that was added to the precessing spins by the first field gradient pulse. However, if the magnetic moments have propagated over a certain distance Δr during that time interval, each precessing spin will have acquired a phase difference Δφ after the second field gradient pulse:

$$\Delta \phi = \gamma t G \Delta r. \quad [13]$$

The measured intensity of the acquired spin echo is a superposition of the projections of the magnetic moments onto the x' (real part of the signal) and y' (imaginary part of the signal) axes of the rotating frame reference.

When the magnetic field gradient has components in all three spatial dimensions, a small elemental volume, dV, of a sample is identified by a common resonance frequency. Assuming that this volume element is located at position r, and that the local spin density at position r is ρ(r), then there will be ρ(r) dV spins in that volume element.

The intensity of the spin echo is determined by three factors:
1. the likelihood of finding a magnetic moment at position r when the first field gradient pulse is being applied,
2. the conditional likelihood that a magnetic moment located at r has propagated a distance Δr during the time interval t' between the onsets of the first and the second field gradient pulses, P(r|Δr,t'),
3. the phase shift Δφ that each precessing spin experiences due to its movement along the direction of the magnetic field gradient.

Since the likelihood of finding a magnetic moment at position r is given by the local spin density ρ(r), the intensity of the spin echo can be calculated:

$$S(\delta, G, t') = \int\int \rho(r) P(r|\Delta r, t') \exp(i\Delta\varphi) dr d\Delta r \quad [14]$$

$$= \int\int \rho(r) P(r|\Delta r, t') \exp(i\gamma \delta G \Delta r) dr d\Delta r$$

Factors 1 and 2 can be combined and are commonly referred to as the self-correlation function $\bar{P}(\Delta r, t')$:

$$\bar{P}(\Delta r, t') = \int \rho(r) P(r|\Delta r, t') dr. \quad [15]$$

Using Equation 11, the NMR signal amplitude may be expressed as:

$$S(t, G, t') = \int \bar{P}(r|\Delta r, t') \exp(i\gamma t G \Delta r) d\Delta r. \quad [16]$$

The product $(2\pi)^{-1} \gamma G t$ is an element of the wave vector, k, and has units of reciprocal space. It determines the spatial resolution of an PFG NMR experiment. The concept of a generalized scattering vector allows applying the formalisms derived for scattering experiments to NMR. Using k, Equation 15 can be rewritten as:

$$S(k, t') = \int \bar{P}(r|\Delta r, t') \exp(2\pi i k \Delta r) d\Delta r. \quad [17]$$

According to Equation 16, the spin echo intensity may be changed by varying either the time (t') or the scattering vector (k) in a PFG NMR experiment. The spin density can be calculated from the measured intensity of the spin echo if the time between the field gradient pulses (diffusion time) is long enough for all spins to have moved to their equilibrium positions. In that case, the likelihood that a particle has moved from position $r_1$ to position $r_2$ is equal to the likelihood of finding a particle at $r_2$, which, in turn, is equal to the spin density at position $r_2$, $\rho(r_2)$. Using Equation 16, and with the annotation that $\Delta r = r_2 - r_1$ it follows:

$$S(k, t_\infty) = \int\int \rho(r_1) \rho(r_2) \exp(2\pi i k (r_2 - r_1)) dr_1 dr_2 \quad [18]$$

$$= \int \rho(r_1) \exp(-2\pi i k r_1) dr_1 \int \rho(r_2) \exp(2\pi i k r_2) dr_2$$

The integral $$S(k, t_\infty) = \int \rho(r) \exp(2\pi i \, k r) dr, \quad [19]$$

is in the form of a Fourier transform of the spin density, which means that for the case of long diffusion times, the observed NMR signal is equal to $$S(k, t_\infty) = I(k) I^*(k) = |I(k)|^2, \quad [20]$$

where I(k) represents the Fourier transform, and I*(k) the conjugated complex Fourier transform of the spin density, ρ(r).

In a two dimensional context, two different imaging techniques are commonly utilized, Fourier Imaging (FI) and Projection Reconstruction (PR), sometimes known as the back projection imaging or inverse radon technique. In PR technique, the object to be studied is first subjected to a magnetic field. A one-dimensional field gradient is applied at several angles, and the NMR spectrum is recorded for each gradient angle.

A first spectrum is recorded with the gradient at zero degrees to the +Y axis. A second spectrum is recorded with the gradient now at a one degree angle to the +Y axis. The process is repeated for the 360° between 0° and 359°. The recorded data can be converted into an image by a 2D Fourier transformation in cylindrical coordinates. Once the background intensity is suppressed, an image can be seen. See, S. R. Deans, S, Roderick, *The Radon Transfer and Some of its Applications*, Wiley, New York, 1983.

Figure 9A:
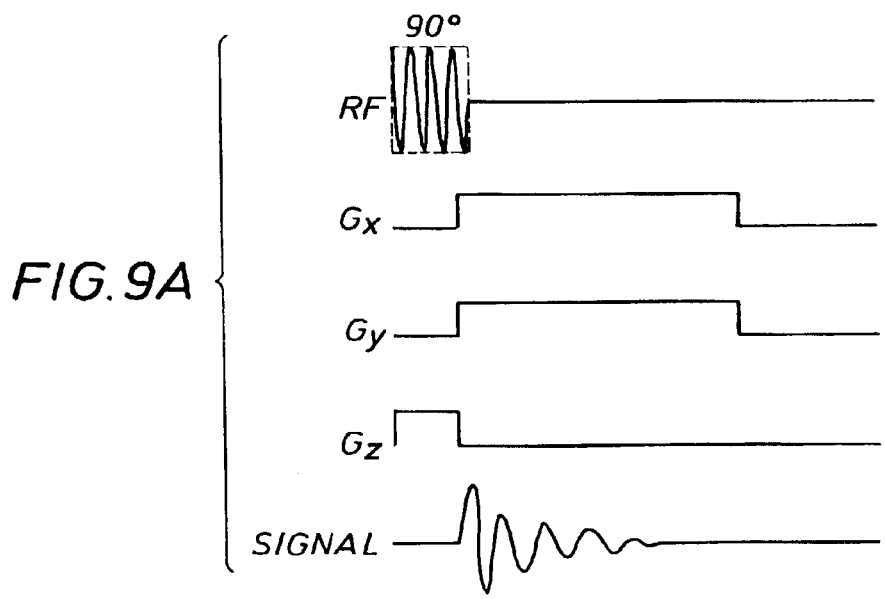
FIG. 9A is a sequence diagram of a projection reconstruction pulse sequence and signal.

In a conventional 90°-FID imaging sequence, the PR technique can be applied utilizing the pulse sequence set forth in FIG. 9A. Varying the angle φ of the gradient is accomplished by the application of linear combinations of two gradients. Here the Y and X gradients are applied in the following proportions to achieve the required frequency encoding gradient $G_f$.

$$G_y = G_f \sin \phi$$

$$G_x = G_f \cos \phi$$

Figure 9B:
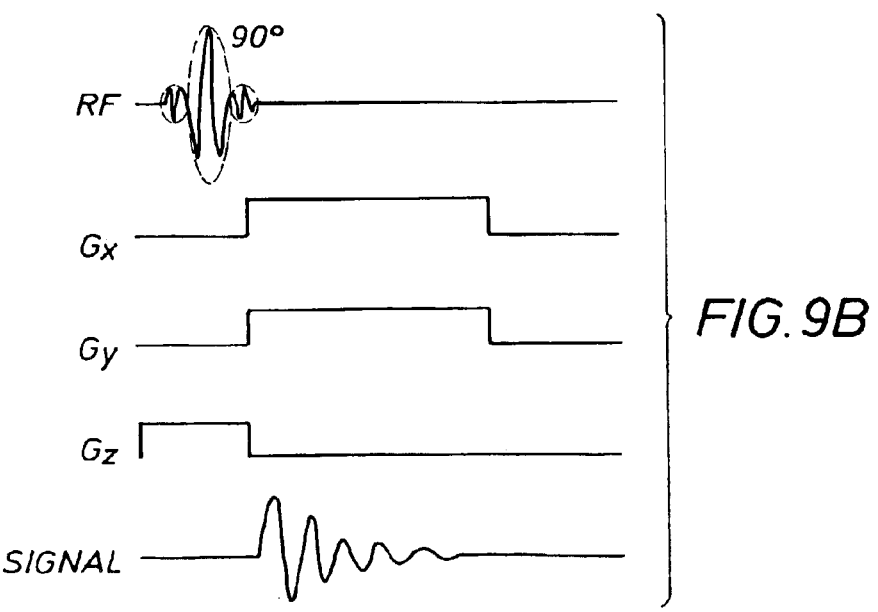
FIG. 9B is a sequence diagram of a Projection Reconstruction pulse sequence and signal, wherein a sinc RF pulse is utilized.

For the PR technique to be a viable imaging technique, it also must be capable of selecting thin slices. This is accomplished by means of the gradient $G_z$, a one dimensional, linear magnetic gradient field, applied orthogonal to the x- and y components of the $B_0$ field during the same period as the RF pulse. A 90° RF pulse applied in conjunction with the $G_z$ magnetic field gradient will rotate spins located in a slice or plane through the object. That can be accomplished with a combination of "hard" and "soft" RF pulses. A "soft" 90° sin pulse contains a small band of frequencies about the desired center frequency. The frequency content of a square 90° pulse ("hard" pulse) is preferably shaped as an apodized sinc pulse, the amplitude of the sinc function being the largest at the frequency of the RF pulse. This frequency will be rotated by 90° while other smaller and greater frequencies will be rotated by lesser angles. The application of a "hard" 90° RF pulse with a magnetic field gradient in the x direction will rotate a broad spectrum of spins in a plane perpendicular to the x axis by 90°. In contrast to this, a "soft" RF pulse will serve as a slice-selective read-out gradient since only spins precessing with a Larmor frequency in the vicinity of the center frequency of the sinc pulse will rotate the magnetic moments. The frequency encoding gradient in FIG. 9B is composed of a $G_x$ and $G_y$ gradient in this example. The FIDs are Fourier transformed to produce the frequency domain spectrum, which is then backprojected to produce the image. A thorough discussion of the 2-D PR techniques may be found in Callaghan, P. *Principles of Nuclear Magnetic Resonance Microscopy*, Oxford Press (1991), pp. 124–28.

While the above example utilizes $G_x$ and $G_y$ for frequency encoding and $G_z$ for slice gradient, the slice, phase and frequency encoding gradients may be selected as indicated in the following table based on the specific sequence being utilized in the NMR/MRI sequence.

TABLE 1

| | GRADIENT | | |
|---|---|---|---|
| Slice Plane | Slice $G_s$ | Phase $G_\phi$ | Frequency $G_f$ |
| X Y | $G_z$ | $G_x$ or $G_y$ | $G_y$ or $G_x$ |
| X Z | $G_y$ | $G_x$ or $G_z$ | $G_z$ or $G_x$ |
| Y Z | $G_x$ | $G_y$ or $G_z$ | $G_z$ or $G_y$ |

By way of example, if the XY slice plane is chosen $G_s$ is $G_z$ and if $G_x$ is selected for phase encoding, $G_y$ will be used for frequency encoding.

This technique could be utilized where the sensor is rotated to change the angle of the gradient to permit the use of back projection techniques in a downhole context.

b. Fourier Imaging Methods

Fourier Imaging (FI) techniques may also be used to image 2-D space. When sampling the FID in the presence of a gradient, signal points are obtained along a single line in k space, which is along the direction of that gradient. In the FI technique, it is generally ascribed to the x-axis. The application of the phase gradient $G_\phi$ imparts a phase modulation to the signal dependent on the position of the volume element along the y-axis. Starting with Eq. 15, above, the signal may be expressed as:

$$S(k_x, k_y) = \int_{-a/2}^{a/2} \left[ \int_{-\infty}^{\infty} \int_{-\infty}^{\infty} \rho(x, y, z) \exp\{i2\pi(k_x x + k_y y)\} dx dy \right] dz \quad [21]$$

where a is the slice thickness. Since it merely represents the averaging of the spin density across the slice, the outside integral may be ignored and it may be expressed as $$S(k_x, k_y) = \int_{-\infty}^{\infty} \int_{-\infty}^{\infty} \rho(x, y, z) \exp\{i2\pi(k_x x + k_y y)\} dx dy \quad [22]$$

and the inverse Fourier transform is then,:

$$\rho(x, y) = \frac{1}{(k\pi)^2} \int_{-\infty}^{\infty} \int_{-\infty}^{\infty} S(k_x, k_y) \exp[-i2\pi(k_x x + k_y y)] dk_x dk_y \quad [23]$$

Figure 10A:
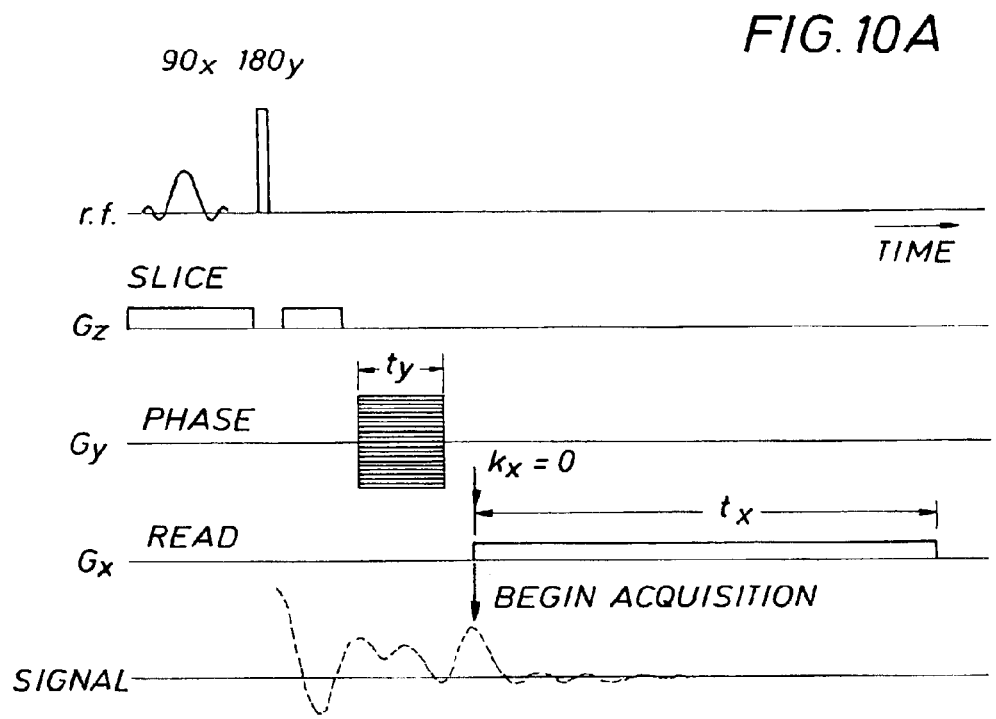
FIG. 10A is a sequence diagram of a two-dimensional Fourier Imaging pulse sequence and signal.
Figure 10B:
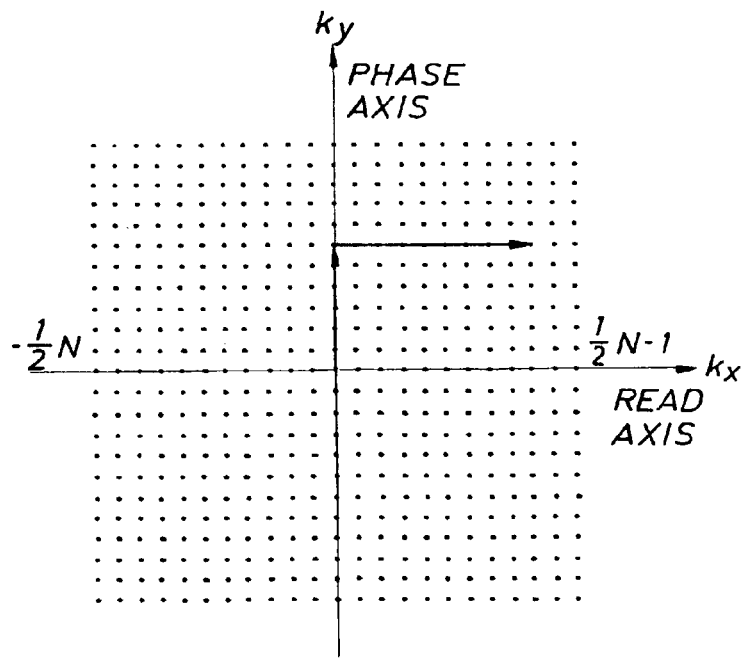
FIG. 10B is the method used for sampling k-space when using the Fourier Imaging sequence.

The 2-dimensional spin density is determined by sampling k space along the x axis under a fixed read gradient $G_z$ for successively increased values of $k_y$. An example of a two dimensional FI pulse sequence and signal is set forth in FIG. 10A, together with the data acquisition sequence for that scheme. In FIG. 10A, a slice selective RF sinc pulse is applied, together with the slice selective gradient $G_z$. A 180° y pulse is then applied to rephase the spins and the slice selective gradient is again applied. The phase gradient $G_y$ is then applied in equal steps across its minimum to maximum value. The frequency or read gradient (sometimes referred to as $G_z$ or $G_f$) is then turned on and a signal is recorded in the form of the Free Induction Decay (FID). The sequence of pulses is typically repeated 128 to 256 times to collect all the data required to produce an image. The effect is to map out the pixels in $k_x$ and $k_y$ space (the first quadrant). Application of a negative slice gradient, together with the varying phase gradient would permit one to map the second k space quadrant. Since the phase encoding gradient is applied with a negative value as well, the third quadrant may be mapped. Lastly, by applying a negative read gradient and a negative phase encoding gradient, the fourth quadrant may be mapped. See, FIG. 10B. When the amplitude is a negative y, the third quadrant is then mapped.

Present day imaging techniques as applied within the medical field utilize 3D techniques and Fourier Transform applications to provide three-dimensional images of objects. See for example, J. Hornak, *The Basics of MRI*, www.cis.rit.edu/htbooks/mri. These techniques typically utilize yet another type of magnetic gradient field, the frequency encoding gradient $G_f$, often called the read gradient, to provide additional information. It is used to impart a specific angle to a transverse magnetization vector. The final transverse magnetization direction is dependent on the initial location of the transverse magnetization vector and subsequently applied gradients. FIGS. 11A–11D illustrate the effect of the application of the phase encoding and frequency encoding gradients on spin. The following illustration has been simplified to ignore diffusion effects and non-homogeneities in the $B_0$ and gradients $G_\phi$ and $G_f$.

Figure 11A:
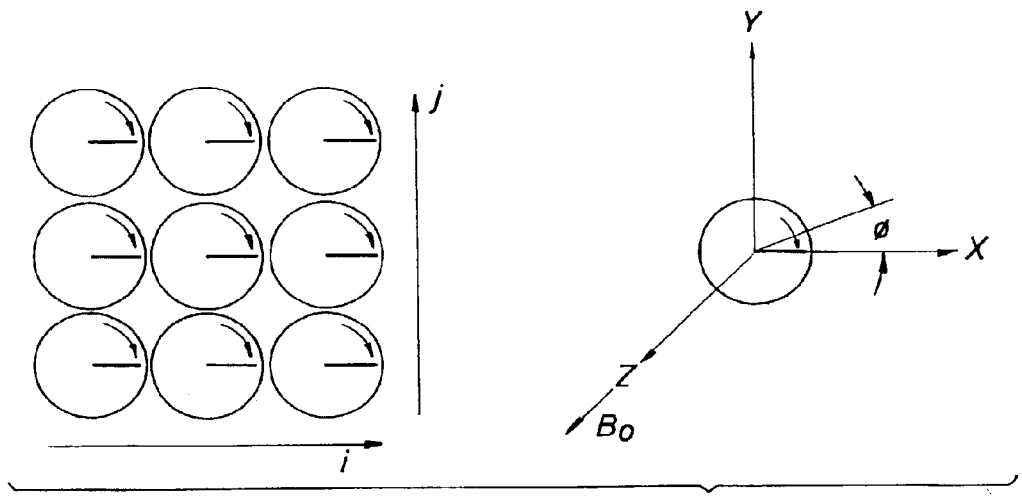
FIGS. 11A–11D are illustrations of the reaction of spin packets to the presence of the $B_0$ magnetic field and phase encoding and frequency/read gradient magnetic fields.
Figure 11B:
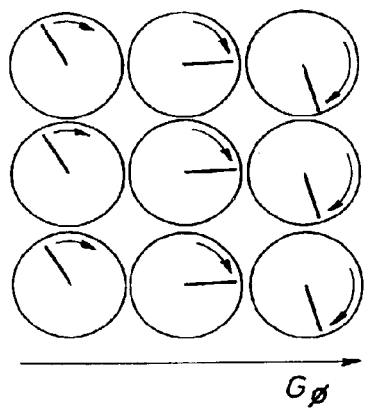
Figure 11C:
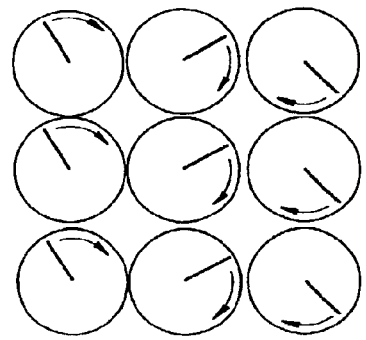
Figure 11D:
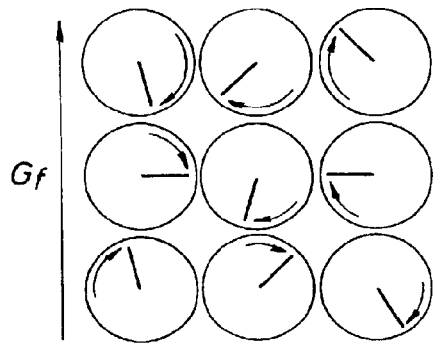

Viewing from the z-axis, and looking down onto the x-y plane, nine different spin packets ($s_{i,j}$), where i=1, 2, 3 and j=1, 2, 3) are selected for a specific slice (following application of an slice selection gradient $G_s$ and slice selection RF pulse) and are subject to a uniform magnetization field $B_0$. FIG. 11A. Since all of the spin packets have the same chemical shift, ideally, they all precess at the same Larmor frequency with respect to each other and the reference packet. FIG. 11A. If a magnetic gradient field (phase gradient $G_\phi$) is applied along the X axis, the nine spin packets will precess at three different rates as function of the direction of the applied $G_\phi$ gradient, as there will be three different Larmor frequencies, as set forth in Equation 8 above. FIG. 11B. The precessional rates in FIG. 11B are indicated by the length of the rotational arrow. Thus, spin packets $S_{1,j}$ have a common precessional rate, as do $S_{2,j}$ and $S_{3,j}$. As $G_\phi$ continues to be applied, the nine spin packets will continue to precess at the three different Larmor frequencies. When the $G_\phi$ is terminated (FIG. 11C), the external $B_0$ magnetic field is essentially homogeneous. The packets will precess at the same Larmor frequency, but having three different phase angles φ, when compared to a reference phase vector, within its own frame of reference. FIG. 11C. In FIG. 11D, a frequency encoding gradient $G_f$ is applied along the y axis. In this instance, the nine spin packets precess at three different Laramor frequencies, with the rate of precession indicated by the length of the rotational arrow. As will be noted, the three spin packets $S_{i,1}$ subject to the strongest gradient all precess at the same rate. The spin packets initially start with their respective phase encoding with respect to a reference spin, but now rotate at a different frequency than the reference packet, which is subject only to $B_0$. The phase angle for each spin packet in row 1 proceeds to change with respect to the reference spin. Each spin packet $S_{i,2}$ likewise starts from its initial phase encoding in FIG. 11B and now precess at a common rate corresponding to its Larmor frequency which differs from the frequency in row 1. At the same time, the magnetization vector for each spin packet $S_{i,2}$ remains different. Lastly each spin packet $S_{i,3}$ starts with its initial frequency encoding from FIG. 11 and all spin packets precess at a faster rate corresponding to its Larmor frequency when compared to spin packets $S_{i,1}$ and $S_{i,2}$ or the reference spin. The nine spin packets in FIGS. 11A–11D each now have a unique magnetization vector and retain this unique vector when the $G_f$ field is turned off, and they all precess at the same rate in the presence of the homogeneous $B_0$ field. The ability to measure magnetization vectors and spin phases for each of the nine spin packets is essential to the use of Fourier Imaging (FI) imaging techniques.

Figure 12:
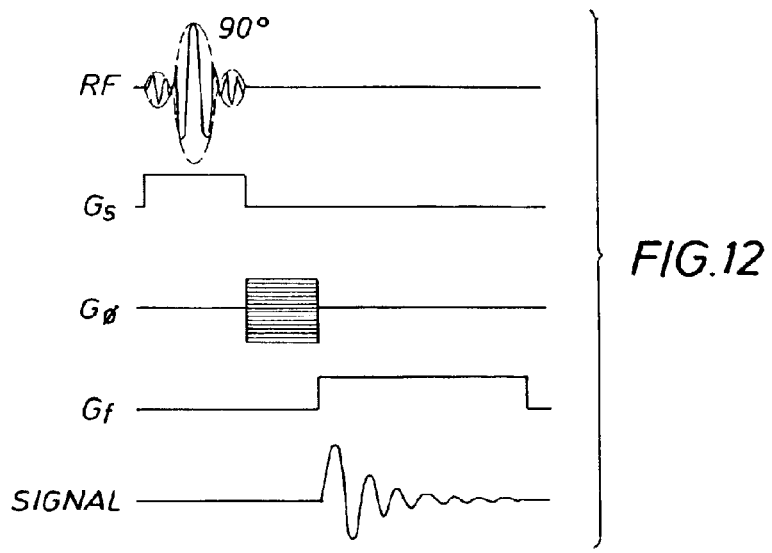
FIG. 12 is a sequence diagram of a sequence used in conjunction with multislice imaging techniques.

Referencing FIG. 12, the simplest 3-D FI imaging sequence is comprised of an apodized 90° sinc RF slice selective pulse, a slice selective $G_s$ magnet gradient pulse, a phase encoding gradient pulse $G_\phi$, a frequency encoding gradient pulse $G_f$ and a subsequent signal, the magnetic gradient pulse sequences representing the amplitude of the gradient pulse and its duration. The slice selection gradient $G_s$ turned off upon completion of the RF pulse and the phase encoding gradient is turned on. Once the slice selection gradient is turned off, the phase encoding gradient $G_\phi$ is turned on. The phase encoding gradient is then turned off and the frequency encoding gradient $G_f$ is turned on and a signal is recorded. The signal is in the form of a FID signal. The sequence is typically repeated numerous times to collect data necessary for imaging purposes. Each time the sequence is repeated, the magnitude of the phase gradient is changed in equal steps between its maximum value $G_{+\phi m}$ and its minimum value $G_{-\phi m}$. The sequence may then be repeated for multiple slices to create a 3-D image of the object.

2. Imaging Sequences a. Multislice Imaging

The basic Multislice Imaging sequence is set forth in FIG. 12. However, it is not practical to attempt to use this sequence in either the medical or borehole environments, where a 90° flip angle is used. The reason is the time required to acquire the necessary information for a data image. An alternative method would be to decrease the pulse angle, e.g., to 10°, thereby decreasing the time required for the sequence. However, in a non-homogeneous field, the spectral width of the object being studied must be less that the spectral width of the pulse, otherwise no FID can be observed. Assuming that the entire FID-based sequence of FIG. 12 can be repeated every 1 seconds and that 256 differing values of the phase gradient are applied, it would take over 4 minutes to acquire the data for a single, small field of view image, where the field of view (FOV) is defined according to the following relationship:

$$FOV = f_s/\gamma G_f \quad [24]$$

The use of smaller pulse angle will substantially reduce the signal recovery time between scans. One other technique that may be used is to reduce the FOV volume being investigated. Where $f_s$ is the sampling rate and $G_f$ is the frequency gradient. Any imaging utilizing this technique would be impractical with a constant logging speed tool. The Multislice Imaging technique maybe improved by utilizing RF pulses having differing frequencies (or center frequencies in the instance of sinc pulses) see FIG. 13. Thus, so long as the respective gradient fields and RF pulses do not overlap, the time required to acquire image data may be substantially reduced when compared with the time for the sequence of FIG. 12. Commercial NMR tools having multi-frequency capability, such as the MRIL-PRIME, may be utilized to perform multi-slice imaging. The time required for this technique may not present a problem when used in conjunction with a formation tester having a long test program (and the tool string is already stationary).

b. Spin Echo Sequence

Figure 14:
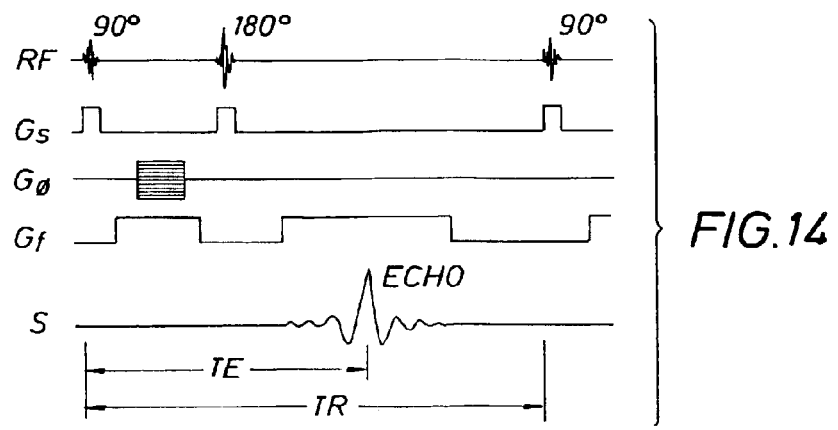
FIG. 14 is a sequence diagram for a basic spin echo sequence.

One of the more commonly utilized MRI imaging pulse sequences is the "Spin-Echo" sequence. The basic Spin-Echo pulse calls for the application of a 90° RF pulse, following polarization of the sample. The 90° pulse flips the nuclei into the transverse (x-y) plane. Following termination of the RF signal, the nuclei begin to dephase and a FID signal is detected. At t=τ, a 180° RF pulse is applied which flips the spinning nuclei 180°, for example, about the X axis and partially rephases the nuclei and produces an echo signal. The pulse sequence and resultant signals are depicted in FIG. 14. The sequence begins with the 90° pulse and simultaneous application of the $G_s$ slice selection gradient. A phase encoding gradient is applied between the 90° and 180° pulses. As with the Multislice imaging technique, the phase encoding gradient is varied in multiple steps between $G_{\phi m}$ and $G_{-\phi m}$. In order to minimize the TE (echo time) a frequency encoding gradient is also applied between the 90° and 180° pulses. This gradient is along the same direction as the frequency encoding gradient and dephases the spins so that they will rephase by the center of the echo. The slice selection gradient is applied in conjunction with the 180° selection pulse. Following the 180° pulse, the frequency gradient is applied during the time that the echo is recorded. The entire process is repeated every TR (Time Repeat) seconds until all the phase encoding steps have been recorded. Again the time required to perform 256 variations in the phase gradient pulse magnitude tends to be time prohibitive, where TR≈$T_1$.

c. Inversion Recovery Imaging

Figure 13:
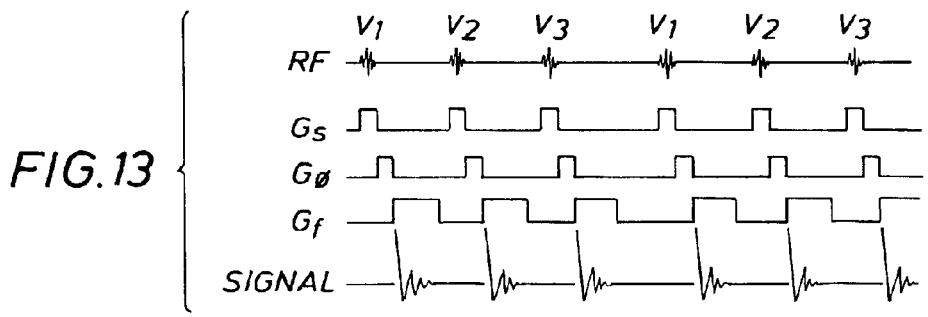
FIG. 13 is a sequence diagram for a multifrequency multislice imaging sequence.
Figure 15:
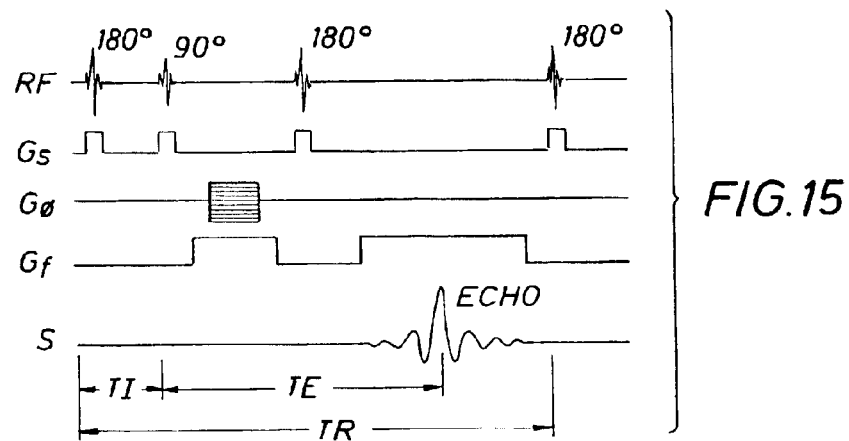
FIG. 15 is a sequence diagram for an inversion recovery sequence.

An inversion recovery sequence utilizing spin echo sequence to detect magnetization may also be used to provide imaging information. In this technique the RF pulses are 180°–90°–180°. The sequence utilizes a 90° FID signal with the exception that a 90° FID is substituted for the spin echo part of the sequence. The sequence is illustrated in FIG. 15. A slice selective 180° pulse is applied in conjunction with the slice selective gradient. The effect of the 180° pulse is to achieve maximum disruption from the equilibrium position induced by $B_0$. When applied in conjunction with the slice selection gradient is operates to suppress unwanted spins. After time TI (Time Inversion), for example, the pulse echo sequence set forth in FIG. 13 is applied. The phase encoding gradient field is again stepped through equal steps between $G_{\phi m}$ and $G_{-\phi m}$ by assigning a different value each sequence. In this instance, the phase encoding gradient is not applied after the first 180° pulse as the spins have not been placed in the transverse plane. The frequency encoding gradient is applied after the second 180° pulse during signal acquisition. The FID signal following the 90° pulse is ignored. The dephasing gradient is applied between the 90° and 180° pulses to assure that they rephase by the center of the echo. The entire process is repeated every TR seconds with a differing phase encoding gradient value. Again, this is a time consuming process that requires stepping through each of the phase encoding gradient values.

d. Gradient Recalled Echo Imaging

Figure 16A:
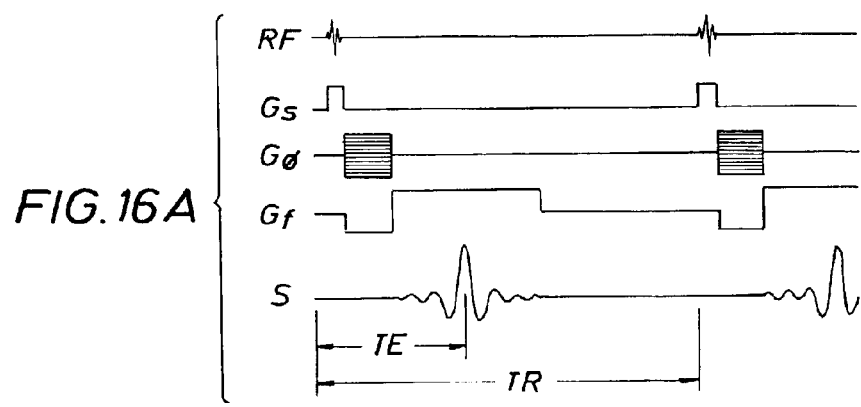
FIG. 16 is a sequence diagram for a gradient recalled imaging sequence.
Figure 16B:
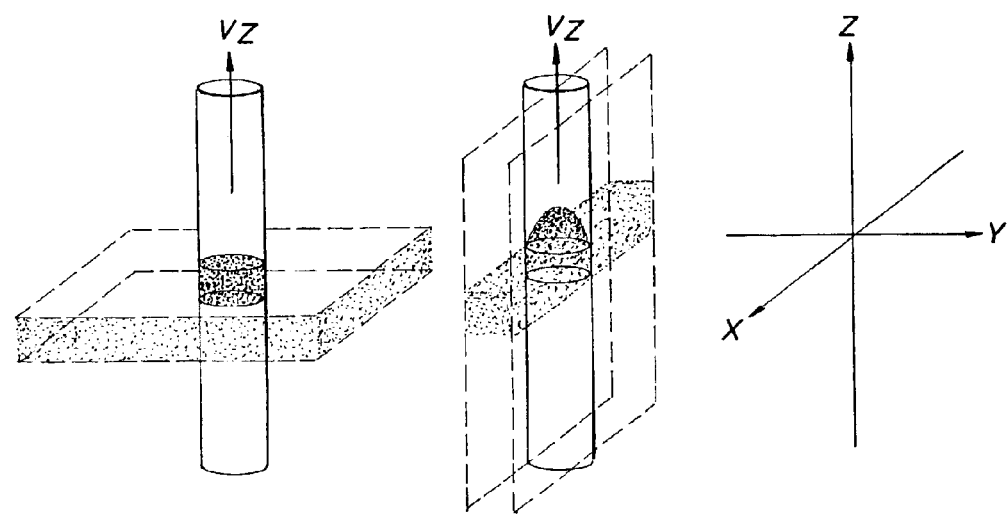

Yet another technique that may be applied in the context of MRI imaging is the gradient recalled echo technique. This technique addresses one problem associated with the previous techniques—the fact that it requires the magnetization to recover its equilibrium position along the z axis. If the $T_1$ time is significant, it will lengthen an already time-consuming imaging process. If the magnetization is rotated toward the transverse plane by an angle θ less than 90°, it will recover equilibrium state, but at the loss of signal strength. It will be appreciated that the loss of signal strength will be proportional to sin θ. This loss of signal may be compensated for by averaging multiple signals for the same area and averaging them together to make up for the loss of signal. The pulse sequence associated with Gradient Recalled Imaging is set forth in FIG. 16. An RF pulse is applied to produce a movement from the gradient equilibrium toward the transverse magnetization plane on the order of 10°–90°, together with a slice selection gradient $G_s$ pulse. Following termination of the gradient selection pulse, a phase encoding gradient is applied, again it is varied in equal steps over the range $G_{-\phi m\ to\ G\phi m}$, a differing value for each sequence. Simultaneous with the application of the phase encoding gradient, a frequency gradient is applied. The frequency gradient is initially applied with a negative value. The frequency gradient is then turned on with a positive value and signal acquisition begins. The effect of initially applying a negative gradient value is to dephase the spins, with the positive pulse rephasing them to produce a maximum signal amplitude at the center of the acquisition period. The echo time TE is defined herein as the time between the start of the RF pulse and the maximum signal amplitude, with the sequence being repeated every TR seconds. Because the sequence does not fully tip the spins into the transverse plane, the time required for the spins to cover and reach $B_0$ equilibrium following the sequence is greatly reduced. As such, TR can be greatly reduced.

As demonstrated above, different techniques may be utilized with a borehole apparatus capable of performing PFG experiments, as were disclosed above. The techniques may be utilized to create near-bore 3-D formation images. Further, the structures disclosed above are capable of performing known NMR/CPMG based logging experiments in addition to the MRI imaging techniques discussed. Thus, the structures above are capable of determining petrophysical properties of the formation as well as being able to image the formation.

3. Flow Imaging

Yet another application of PFG imaging techniques within the present invention is the ability to image connate fluid flow within the formation. In order to image flow, a flow must be induced within the formation and may be accomplished by means of a formation test tool, drill stem tester, or other device to create flow within the formation. The ability to image this flow yields a far more accurate estimate of in situ permeability that does not depend on the particular flow model (laminar, spherical).

As noted above, one use of the present invention would be in conjunction with a formation test tool. A flow would be induced by the formation tester and the MRI sensors used to determine the fluid characteristics and the imaging of the fluid itself as it flows through the formation. Flow imaging, also referred to as angiography, was pioneered in the medical arts field for the imaging of blood as it flowed through a patient's arteries and veins. It will be appreciated that the very same techniques may be utilized to image fluids flowing from the formation into the formation test tool. There are several angiography techniques that have been applied to the medical arts, each of which is discussed herein.

a. Time of Flight Angiography

Figure 17A:
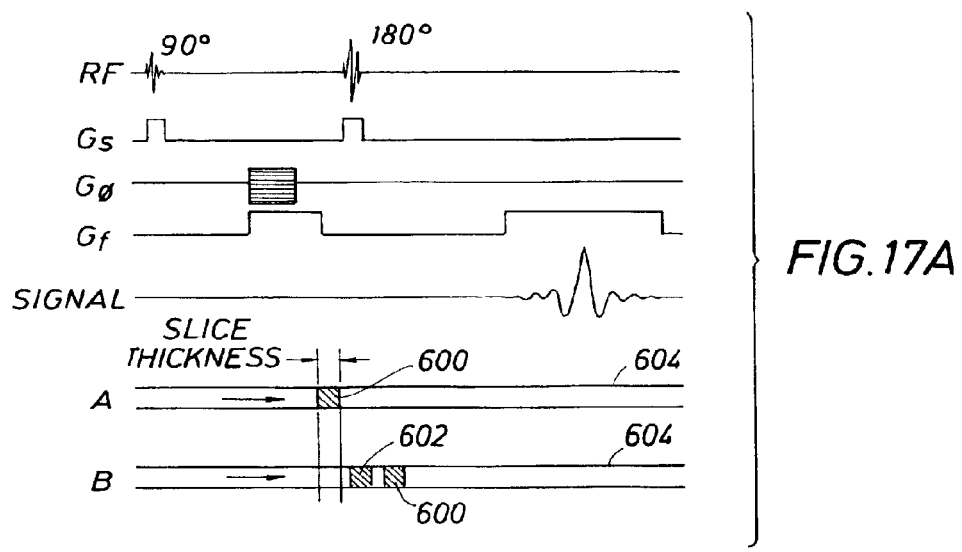
FIGS. 17A–17B are sequence diagram and depiction of a multifrequency, multislice, angiography imaging technique and the manner of slice selection.
Figure 17B:
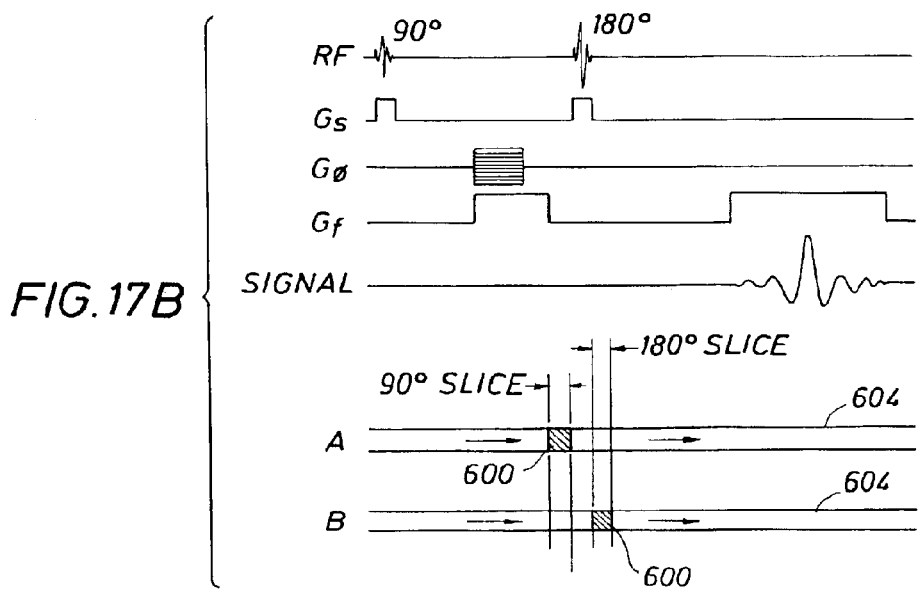

Time of flight (TOF) angiography is also referred to as "spin tagging" and is the most common form of angiography utilized within the medical field. There is no single technique for carrying out TOF angiography. One technique utilizes a spin echo sequence where a 90° slice selective pulse is applied followed by a 180° slice selective pulse having a differing frequency. The net effect would be to have two differing slices. Referring to FIG. 17A, the activation of the various pulse sequences are depicted along a common "time line" with the movement of fluid through a formation. In FIG. 17A, a 90° slice selection RF pulse and a slice selection gradient $G_s$ are applied. The phase encoding gradient $G_\phi$ and the frequency (or read) gradient $G_f$ are applied after the 90° RF pulse and the slice selection gradient. The slice selection gradient and pulse excites the spins within the target slice 600 within the flow path 604, in time line A. As the energized spin packet flows along flow path 604, the phase and frequency gradients are applied. When the 180° RF pulse is applied, it is applied to a packet 602 that was not subject to the initial gradients and 90° RF pulse. While the FID signal may be detected, no echo signal will be detected In order to overcome this, the frequency of the 90° RF pulse differs from that of the 180° RF pulse. The effect is to make two different slice selections, with the 180° RF pulse slice selection following the 90° slice in the direction of the flow. As seen in FIG. 17B, the 90° RF pulse is applied, together with the slice selection gradient $G_s$. The spin packet 600 within the 90° slice thickness is moved to the transverse plane. This is followed by the application of the phase encoding and read gradients. When a 180° RF pulse of a differing selected frequency is applied, the spin packet 600 which has begun to dephase is within 180° slice (line B), the spin packet continues in the direction of flow and the frequency $G_f$ or read gradient is applied and the echo signal is detected.

It will be appreciated that if the spin packets energized by the 90° RF pulse are not subjected to the 180° pulse, that no echo signal will be detected. Likewise, unless the packet 600 subjected to the 180° RF pulse has been moved into the transverse plane by the 90° pulse, no echo signal will be detected. Further, if there is no flow, the 90° RF excited spin packets will not move into the slice thickness for the 180° pulse.

Figure 18:
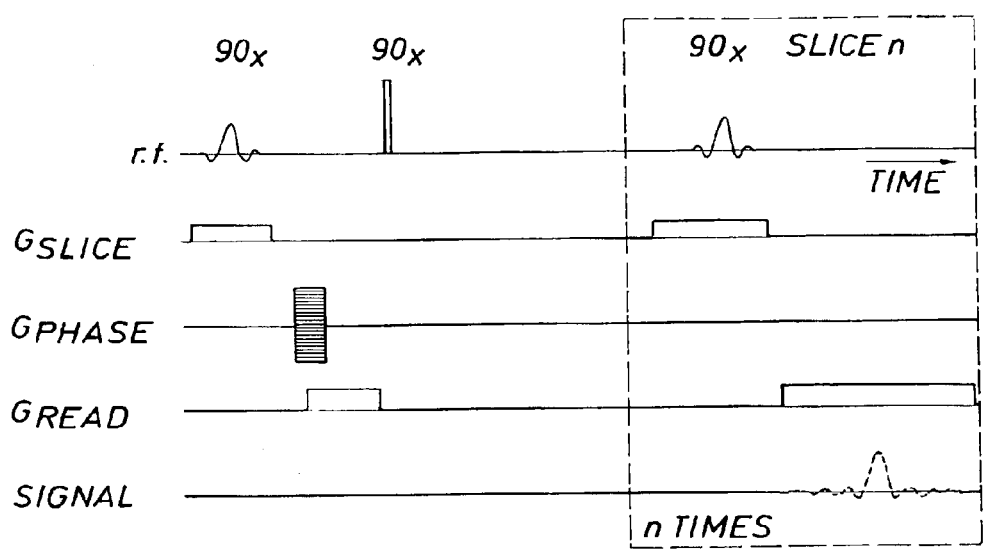
FIG. 18 is a sequence diagram of a single frequency angiography sequence.

Another technique permits the use of a single frequency/ same slice selection is the use of successive interrogations of the selected slice in multiple pulse train utilizing a stimulated echo imaging sequence variant. As set forth in FIG. 18, a 90° RF sinc pulse is applied in conjunction with a $G_s$ slice selection gradient. This is followed by the application of a $G_\phi$ phase encoding gradient, together with a frequency/read gradient $G_f$. Following application of the read gradient, a square 90° RF wave pulse is applied. A sequence consisting of a 90° RF sinc pulse, applied in conjunction with a $G_s$, selection gradient is applied, followed by a $G_f$ read gradient during which time the signal is acquired. By repeating the final sequence, the motion of the target slice is successively followed in a single phase encoding experiment. The entire sequence is then repeated with a differing phase encoding gradient $G_\phi$. The signal intensity is then plotted against time, from which the velocity is determined, given the tagging and slice selection separation. In this instance, the imaging resolution is limited by the slice thickness. The stimulated echo method further offers the advantage that a normal spin density image can be obtained by utilizing the spin echo (not shown) that arises between the second 90° RF spike pulse and the third 90° sinc pulse. The specific timing techniques are well known and are set forth in Merboldt, K., et al. *Journal of Magnetic Resonance*, Vol. 67, p. 336 (1986). What is clear is that the above techniques are limited in terms of the velocity ranges. Since a typical slice thickness for these techniques is on the order of 100 μm and the observation time at about 100 ms, the observable velocities are in the range of 1 mm/sec or greater. It will be appreciated that flow rates seen in a formation may not be within the observable range of flow velocities.

TOF techniques may be utilized to measure flow velocities in response to formation test tool fluid withdrawal. Moreover, the existence of known spin echo imaging techniques, e.g., phase alternated CPMG sequences may be used to determine the fluid characteristics.

b. Phase Encoding Angiography

Figure 19:
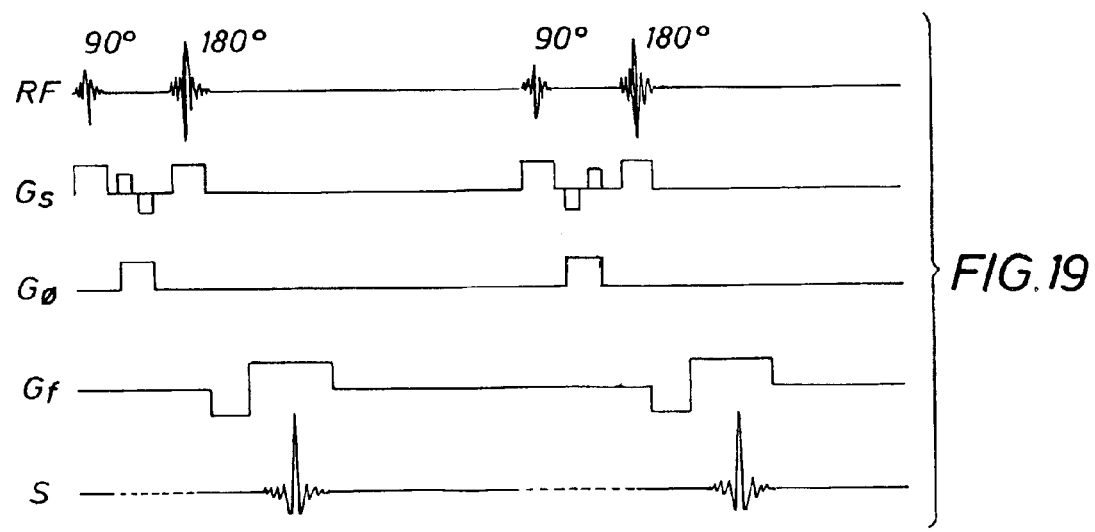
FIG. 19 is a sequence diagram of a phase encoding angiography sequence.

A different technique used to establish flow rates is known as phase encoding or phase contrast angiography. This techniques used differ substantially from the TOF techniques described above and utilize the application of a bipolar gradient G* between the slice selection and imaging sequences, and derives the flow velocity from transverse magnetization phase shifts. A bipolar gradient pulse is one in which the gradient is turned on having a positive or negative amplitude, then turned on in the opposite amplitude for the same period of time. Where the initial lobe is negative, the gradient is described as a negative bipolar gradient; where the initial lobe is positive, it is described as a positive bipolar gradient. This bipolar gradient imposes a phase shift on the spin packet that is dependent on the net spin displacement occurring over the time period of interest. The gradient G*(t) may be made sensitive to velocity, acceleration or higher derivatives or displacements. See, Moran, P. R., et al., *Technology of Magnetic Resonance*, p.149 (1984); Nishimura, D. G., et al., *IEEE Transactions of Medical Imaging*, MI-5, p. 140 (1986). The effective phase shift experienced at time t by a spin I following the path $r_I(t')$ in a gradient field g(t') can be expressed as:

$$\phi_i(t) = y \int_0^t G(t') \cdot r_i(t') dt' \quad [25]$$

Where all the spins have a non-Brownian motion, e.g., a constant velocity, Eq. 24 may be simplified, given constant velocity v, then $r_j(t')$ is reduced to $r_j(0)+vt'$. Similarly, where the flow is undergoing a constant acceleration, $r_j(t')$ can be expressed as $r_j(0)+vt'+\frac{1}{2}at'^2$. The resulting phase shifts involve successively higher moments of G*(t). The zeroth moment must be equal to zero if the final phase shift depends only on the motion and not on the starting position of the spins. Therefore, by choosing the particular time dependence for G*(t), the spin echo signal may be made sensitive to velocity or acceleration of the flow. In most oilfield applications, the flow velocity and not acceleration or some higher order of displacement is of primary interest. However, acceleration information could be used to model transient flow characteristics of the formation that may then be used in the study of the anisotropic permeability of the formation. The gradient modulation may be produced by an opposite sign pair as shown in FIG. 19, or by a pair of identical pulses separated by a phase-inverting 180° pulse. If the mean velocity over time t for spins in a position r is v, then the induced phase shift for that position/voxel may be expressed as exp [ip·v(r)], where p is the velocity encoding gradient $\phi_r(t)$ for a non-zero first moment.

One pulse sequence for flow imaging of a constant velocity flow is depicted in FIG. 19. A 90° RF sinc slice selective pulse is applied together with the slice selection gradient $G_s$. Thereafter, a positive bipolar $G_s$ gradient is applied together with the phase encoding gradient $G_\phi$. The $G_s$ slice selection gradient is applied again with a 180° RF sinc pulse, followed by the application of a negative amplitude read/frequency gradient (to dephase the spins) and an immediate application of a positive amplitude read gradient during signal acquisition (again rephasing spins, thereby ensuring maximum amplitude at the center of the acquisition period). The sequence of FIG. 19 is then repeated but with a negative bipolar pulse. When the raw signal from the positive and negative bipolar sequences is subtracted and all of the stationary spin signal is cancelled, the remaining signal is attributable solely to the constant flow spins. Other pulse sequences and means of achieving signal cancellation attributable to stationary spins may be found in Callaghan, P. T., *Principles of Nuclear Magnetic Resonance Microscopy*, pp. 429–34, Oxford Press (1991). When angiography techniques are applied to formations in conjunction with formation testers, and their induced flow, the MRI device, as depicted in FIGS. 3 and 4, may be used to accurately measure the flow of the fluids within the formation. Further, the same structures may be utilized to perform conventional CPMG experiments to determine formation characteristics and fluid typing. See, e.g., Coates, G. R., et al., *NMR Logging Principles and Applications*, pp. 77–90, Halliburton Energy Services (1999).

c. Velocity and Diffusion Determination

The phase encoding techniques applied above may be further processed to determine not only the velocity of the flow of the connate fluids, but the self-diffusion of the fluids themselves. This is done utilizing a combination of k space and q space imaging. This combined imaging technique is generally referred to as dynamic microscopy. Recall that the concept of k space imaging was first discussed with respect to Fourier Imaging techniques above and represents a means for interpreting the received NMR signal, where:

$$k = (2\pi)^{-1} \gamma G t \quad [26]$$

where G is a component of the gradient. For experiments with field gradient pulses of a certain duration, δ, a reciprocal space vector q is similarly defined by:

$$q = (2\pi)^{-1} \gamma \delta G = \frac{1}{\Delta} \int_0^t G(t') t' dt' \quad [27]$$

where G is the effective intensity of the pulsed field and Δ represents the time differential between the centers of two antiphase pulses in a gradient pulse pair.

Figure 20:
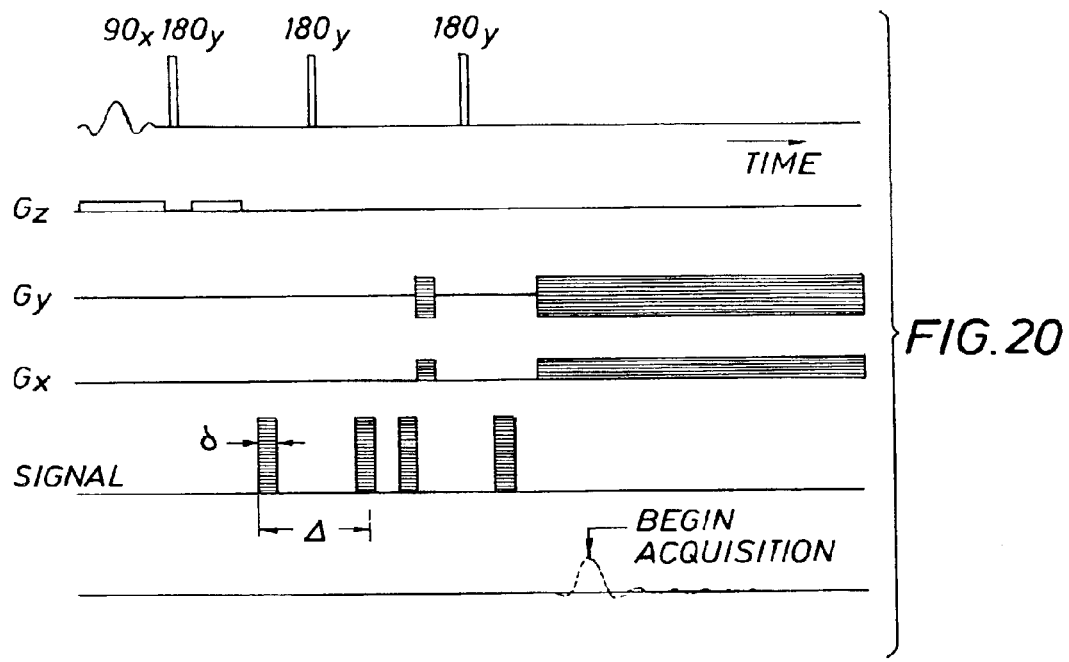
FIG. 20 is a PGSE pulse sequence that may be used to detect fluid flow.

The pulse sequence for dynamic microscopy shown in FIG. 20 is an example of a PGSE or pulsed gradient spin echo sequence. In this sequence, a 90° RF sinc pulse is applied in conjunction with the slice selection gradient. A 180° rephasing square pulse is applied, followed again by the application of the slice gradient. A PGSE phase gradient is then applied at varying values up to some maximum value g for a period δ. A rephasing 180° square pulse is again applied followed by the application of two phase gradient sequences. This effectively eliminates the velocity encoding and encodes the fluctuating component of the velocity or acceleration. The effect of the phase encoding sequences herein is to phase encode the fluctuating component of velocity in q space while preparing to sample k space. Again, G has a different value applied in equal steps to its maximum value. The phase encoding $G_y$ and frequency encoding $G_x$ gradients are then applied for varying values, the x gradient for different positive x-values, the y values for both negative and positive values and the signal is obtained.

The signal obtained from the PGSE imaging pulse sequence of FIG. 20, for a single PFG pair may be expressed as:

$$S(k,q) = \int \rho(r) \exp[i2\pi k \cdot r] \int P_s(r|r',\Delta) \exp[i2\pi q \cdot (r-r')] dr' dr \quad [28]$$

where $P_s(r|r', \Delta)$ is the conditional probability that for a spin originating at time r will move to position r' during the diffusion time between the onset of the two field gradient pulses, Δ. Equation 24 can be simplified for experiments with pulsed field gradients by use of the echo attenuation function, $E_A(q,r)$. Since in that experiment, the field gradient pulses can be switched off, the intensity of the spin echo with field gradient pulses being applied can be normalized to the intensity of the spin echo without any applied field gradient pulses switched on during the experiment. For stationary particles, $E_A(q,r)$ will have a value of unity, while diffusion molecules will reduce $E_A(q,r)$ to values smaller than one. This procedure cancels all relaxation effects which otherwise would also contribute to the attenuation of the spin echo amplitude.

The echo attenuation function as a function of q space and position r in time Δ may be expressed as:

$$E_A(q,r) = \int P_s(r|r',\Delta) \exp(i2\pi q(r'-r)) dr', \quad [29]$$

which is the q Fourier transform of the local conditional probability that a particle has moved from position r to position r' during the time Δ.

Relating Equation 25 to Equation 24, the signal intensity measured with a PFG NMR imaging sequence may be written as:

$$S(k,r) = \int \rho(r) E_A(q,r) \exp[i2\pi k \cdot r] dr \quad [30]$$

In reviewing Eq. 26, the reconstruction of the signal in k space can be expressed as ρ(r) $E_A$(q, r), which will provide a diffusion-weighted spin density at position r. The q Fourier transform of the local conditional probability set forth in Eq. 25 calls for an infinitesimal volume dr, which as a practical matter, is averaged over some 3d voxel. Given this background, one may measure both velocity, acceleration and self diffusion of the molecules being studied.

Figure 21:
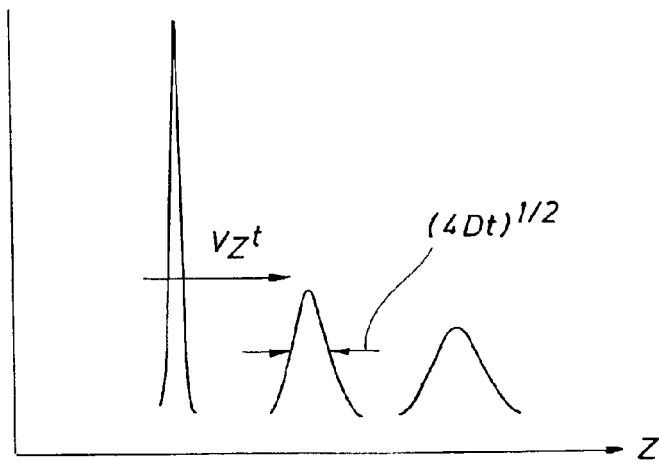
FIG. 21 is a depiction of the behavior of the conditional probability functions $P_S$ for the behavior of particles in response to Brownian motion and flow.

FIG. 21 illustrates the conditional probability function $P_s$. A velocity and a diffusion map for each voxel may be obtained by computing the width and offset of $P_s$ in Z space. In practice, dynamic profiles are obtained by stepping the PGSE gradient G in $n_D$ steps to some maximum value $G_m$, followed by performing a digital Fourier transform in q space for each voxel. As noted in Callaghan, P., *Principles of Nuclear Magnetic Microscopy*, Oxford University Press (1991), it may then be derived that the mean molecular velocity for the voxel is $$v = 2\pi n_D k_v / N \gamma \delta \Delta G_m \quad [31]$$

where N is the number of time domain points digitally sampled. The diffusion value is then expressed as:

$$D = (n_D k_{FWHM})^2 / ((4 \ln(2)/\pi^2) \gamma_2 \delta^2 G_m^2 N^2 \Delta) \quad [32]$$

where $k_{FWHM}$ represents the full-width, half maximum value in displacement space in the Z direction. See, FIG. 22. This is simply one technique by which one can determine both velocity of the flow and the self-diffusion of the molecular flow.

d. Position Exchange Spectroscopy (POXSY).

Yet another means for determining fluid flow characteristics is the use of position exchange spectroscopy (POSXY) 2-D Fourier Transform techniques. A POSXY experiment recognizes that the amplitude of the echo is a function of the area of two differing field gradient pulses. Since the area of the field gradients are related to the length scale, a 2-dimensional plot results in a probability density of finding a particle at position 1 at time 1 and at position 2 at time 1+diffusion time. This allows one to map the change of position of particles within the diffusion time. A POSXY experiment provides a correlation diagram of the average position with displacement by using pure phase encoding techniques.

4. "Real Time" Imaging Techniques

The imaging techniques discussed above are applicable where the MRI apparatus stationary (in the instance or a formation tester or drill stem tester) or moving at a relatively slow logging speed. Again, the logging speed is limited by the recovery times associated with the above techniques. It will be appreciated that MRI logging techniques are more likely to be a commercial success where they can be applied at or near current logging rates, e.g., 30+ ft./min. In order to achieve MRI faster scan (and logging) times, one must consider what factors go into limiting scan time. Spin echoes are usually quite brief in nature and to a great extent are limited by $T_2$ times. Table 2 sets forth typical $T_1$ and $T_2$ times encountered in the well logging context.

TABLE 2

| Fluid | $T_1$ (ms) | $T_2$ (ms) | $T_1/T_2$ |
|---|---|---|---|
| Brine | 1–500 | 1–500 | 1 |
| Oil | 3,000–4,000 | 300–1,000 | 1 |
| Gas | 4,000–5,000 | 30–60 | 0.2–0.4 |

Source: G. R. Coates, et al., NMR Logging, Principles & Applications, Halliburton Energy Services, p. 78 (1999).

The necessary molecular spatial encoding required to form an image cannot usually be performed in the above time periods. Accordingly, the sequences are repeated until there is sufficient data to complete any image. Of course, when the sequences are repeated, the signal amplitude is reduced. Eventually the S/N ratio is so low that the formation under investigation must eventually undergo total remagnetization before additional signal can be obtained. However, the remagnetization of the molecules is limited by $T_1$. It will be appreciated that many of the techniques set forth above would requires several seconds at each location in the borehole.

Several imaging techniques have been employed in the medical field to allow for near real time video imaging. These are generally a combination of pulse sequences, the manner in which k-space is sampled and methods used to improve the S/N ratio. The scan time for a volume is generally follows:

$$\text{ScanTime} = TR \times \text{Number of Phase Encodes} \times NEX \quad [33]$$

where TR is the repetition time between successive RF pulses; Number of Phase Encodes which determines spatial resolution; and NEX is the number of averages of the data required to form a sufficiently noise free image.

One means of reducing TR is to reduce the transverse angle θ from 90° to a lesser angle. This technique was already touched on in the above discussion of Gradient Recall Echo Imaging. The smaller θ, the less time required for remagnetization (effectively decreasing $T_1$) times; however, it also decreases, the strength of the signal received in response to the RF pulses. It will be appreciated that merely reducing θ to less than 5° will have an adverse affect on the NEX value. This reduced θ forms the basis for FLASH techniques.

a. FLASH Techniques

Figure 22:
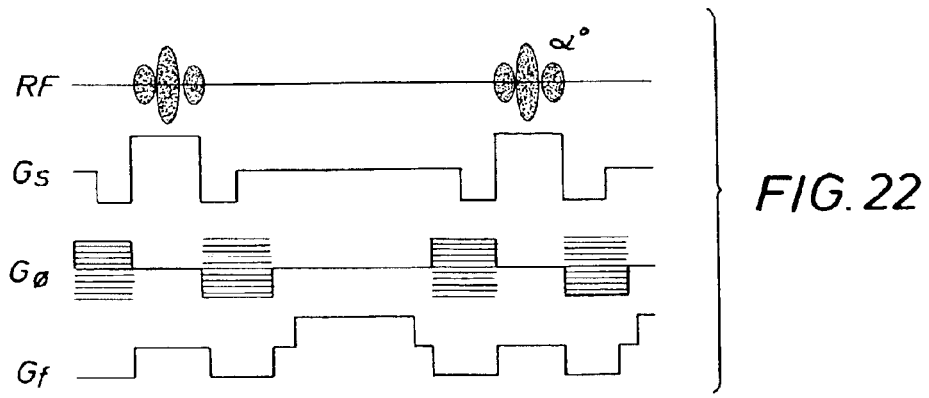
FIG. 22 is a depiction of the FAST SSP sequence that may be used for image acquisition.

FLASH (Fast Low Angle SHot) techniques were introduced into the medical field as a means of obtaining complete imaging scans in the tens of seconds. In FLASH techniques, the low angle excitation is used to sweep an entire k space in a relatively short period of time. With repetitive reading and relatively small $TR/T_1$ times, the FID signal amplitude may be expressed as:

$$M_y = M_0 \cos^n\theta \sin\theta \qquad [34]$$

where n is the number of times RF pulses are used to move spins to angle θ. As noted above, the low θ value adversely effects the S/N ratio. FIG. 23 is a sequence diagram for a FLASH technique that utilizes a "rewinding" phase gradient in each cycle. The RF pulse is applied along with the $G_s$ slice gradient, that changes sign to refocus the spins. The phase gradient is applied in equal steps from its $-G_{\phi M}$ to its $G_{\phi M}$; simultaneously, the read gradient is turned on with a negative sign to assure that the echo will be centered in the if the read period when the read gradient is turned positive. The sequence ends with the phase gradient "rewinding" the spins by applying it from $G_{\phi M}$ to $-G_{\phi M}$. The sequence is then repeated n times. The particular sequence shown in FIG. 22 is sometimes called a FAST SSFP (Steady State Free Precession) is that by applying the rewinding gradient, the transverse coherence of the spins is retained to create a steady state free precession.

The result is that a complete sampling of k-space for a FLASH image can be accomplished in less than a second. There are a number of differing low angle techniques that may be used to decrease the TR time necessary to complete a scan. Other low δ sequences include CE-FAST, FISP, FADE, Turbo FLASH and can be used to reduce the scan times to less than a second for small areas of investigation. A detailed discussion of the various high speed/low angle techniques may be found in M. Cohen, *Rapid Imaging: Techniques and Performance Characteristics*, Radiology, Lippincott, New York, N.Y. (1992).

b. K-Space Rapid Sampling Techniques

In an effort to decrease the k-space sampling time, partial k-space sampling techniques may be used. MRI sequences measure the complex matrix, $I(k_X, k_Y)$. In the absence of noise and other artifacts, the image matrix in k-space may be expressed as follows:

$$I(k_X, k_Y) = I^*(-k_X, -k_Y) \qquad [35]$$

Under these conditions, only half of the matrix need be measured and the other half can be inferred. As a practical matter, noise, field non-homogeneities, and sample effects introduce a phase variation across the matrix introduces error into the sampling. Corrections can be made by sampling into the second half of the matrix and assuming the phase variation to be linear, and applying it to the inferred data. Two common techniques used for partial k-space sampling are the Fractional Echo, and Fractional NEX Imaging. The Fractional Echo imaging technique is typically utilized in conjunction with a spin-echo sampling sequence. The Fractional Echo technique focuses on shortening the minimum echo time $T_E$ and may be used with techniques such as FLASH for rapid acquisition. Filling the k space data matrix column by column, the remaining data is extrapolated in the matrix using the technique as follows:

$$\begin{bmatrix} k_{11} & k_{12} & k_{13} & k_{14} \\ k_{21} & k_{22} & k_{23} & k_{24} \\ k_{31} & k_{32} & k_{33} & k_{34} \\ k_{41} & k_{42} & k_{43} & k_{44} \end{bmatrix} = \begin{bmatrix} k_{11} & k_{12} & * & * \\ k_{21} & k_{22} & * & * \\ k_{31} & k_{32} & * & * \\ k_{41} & k_{42} & * & * \end{bmatrix} \qquad [36]$$

where * is the calculated complex conjugate value $-k_{JI}^*$.

Fractional NEX Imaging or Half NEX techniques may also be used to sample k-space and reduce the time required. In reviewing the k-space image, the matrix $I(K_X, K_Y)$ can be expressed as follows:

$$\begin{bmatrix} k_{11} & k_{12} & k_{13} & k_{14} \\ k_{21} & k_{22} & k_{23} & k_{24} \\ k_{31} & k_{32} & k_{33} & k_{34} \\ k_{41} & k_{42} & k_{43} & k_{44} \end{bmatrix} = \begin{bmatrix} k_{11} & k_{12} & k_{13} & k_{14} \\ k_{21} & k_{22} & k_{23} & k_{24} \\ * & * & * & * \\ * & * & * & * \end{bmatrix} \qquad [37]$$

where * is the calculated complex conjugate value $-k_{JI}$. Thus, in the example, only $k_{11}$-$k_{24}$ need actually be sampled, requiring only half of the time.

c. SPRITE Techniques

Figure 23A:
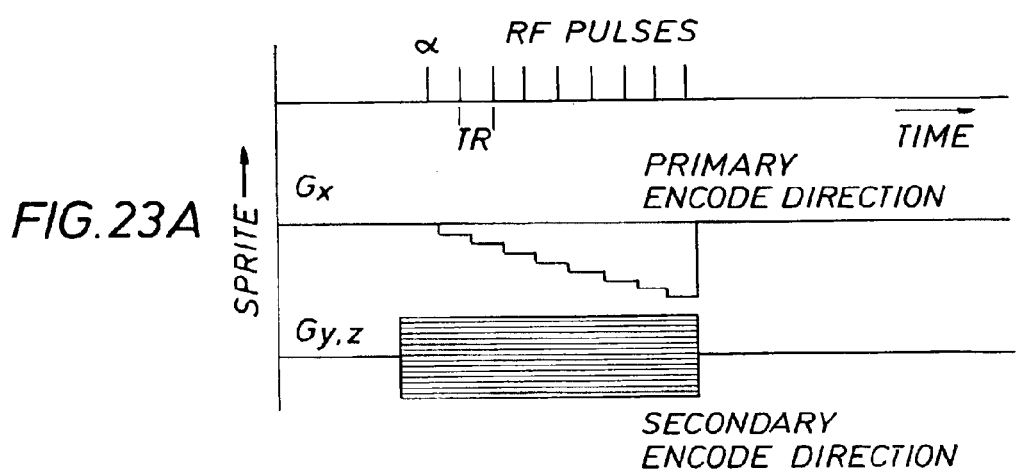
FIGS. 23A and 23B are depictions of two different SPRITE sequence techniques that may be used for image acquisition.
Figure 23B:
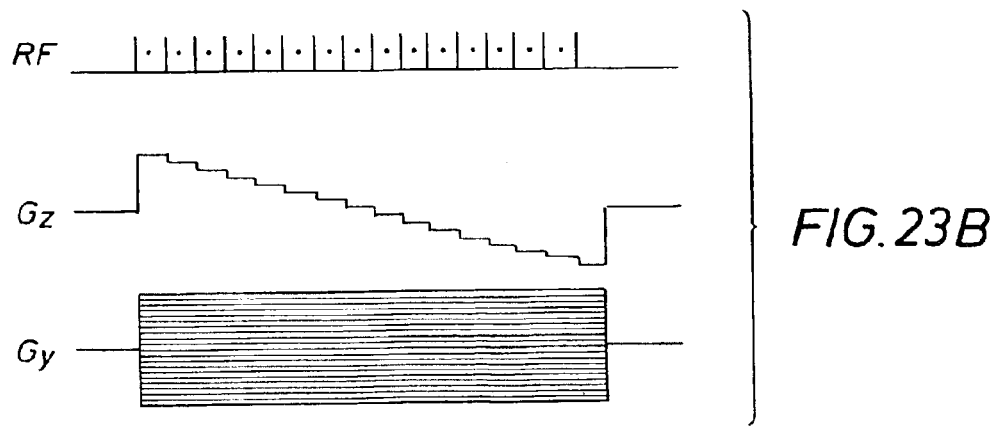

Yet a different means for creating essentially real time images for fluid evaluation is the use of the SPRITE (Single Point Ramped Imaging with $T_1$ Enhancement). FIG. 23A is a depiction of a SPRITE sequence. SPRITE is a pure phase encoding Fourier Transform method that employs broadband RF pulses to excite magnetization and a ramped gradient in the primary phase encode direction (in this instance $G_X$). The steps in this $G_X$ gradient typically last only a few milliseconds. K-space is sampled on a point by point basis. It will be appreciated that k-space sampling techniques discussed above may be used to decrease the sampling time. FIG. 23B is a depiction of this modified k-sampling technique in which slice selection is used to spin lock the transverse magnetization for subsequent readout. Thus, only half of the k-space is sampled.

These rapid imaging techniques are capable of providing real time angiography information relating to the flow of fluid within the formation as well as borehole imaging. It will be further appreciated that these techniques may be used in addition to known NMR techniques within the well borehole.

5. Background Gradient Suppression

The above discussion relating to positional measurement and self diffusion are within homogeneous systems wherein $T_1 \gg T_2$. However, such is not always the case in the formation. However, in heterogeneous systems that have components with differing magnetic characteristics, a distribution of spatially dependent background gradients for the differing components may result in attenuation of the echo signal and the introduction of systematic error in the measurement of diffusion. Specifically, the background field inhomogeneities can cause a decrease in the observed $T_2$ times through the effects of translational diffusion of the spins. In severe cases, it could result in erroneous modeling of the formation or prevent the use of NMR techniques altogether Several PFG sequences have been proposed to address these background gradients. Specifically, the use of an alternating bipolar gradient pulse to minimize the effects of the cross term ($G_a G_0$) created by the applied gradient $G_a$ and the background gradient $G_0$. Several of the techniques for suppressing background gradients were discussed in Cotts, R. M., et al., *Pulsed Field Gradient Stimultated Echo Methods for Improved NMR Diffusion Measurements in Heterogeneous Systems*, Journal of Magnetic Resonance vol. 83, pp. 252–66 (1989). The paper therein discusses the "nine", "thirteen" and "seventeen" interval Hahn sequences, also known as Carr Purcell PFG sequence, utilizing bipolar gradients. It describes the spin echo factors in terms of the total effective gradient g(t).

$$k_p = \gamma \int_0^{t_a} G(t)dt \quad [38]$$

and $$k_r = \gamma \int_{t_b}^{t_c} G(t)dt \quad [39]$$

In attempting to minimize the cross terms attributable to the background gradient, each of the sequences discussed in the paper has two solutions:

$(k_p - k_r) = 0$           Condition I:

$(k_p + k_r) = 0$          Condition II:

In FIGS. 24A and B, an illustrative thirteen interval sequence is set forth. In FIG. 24A, the true laboratory gradient is set forth for Condition I. It will be noted that the effective gradient is the same during the preparation period as during the read period of the sequence. FIG. 24B represents the applied polarities of the system. As in the true gradient illustration, the effective gradient is similar during the preparation and read phases of the sequence. As noted therein (See Eqs. [3]–[12]), the echo amplitudes for the various sequences each includes a cross term $G_a G_0$. By selection of the interval following the various pulse sequences and the selection of the length of the gradient pulse, one can minimize the effect of the cross term. With respect to a thirteen interval sequence, the echo amplitude may be expressed as:

$$\ln\left[\frac{m^I(G_a, t_c)}{m^I(0, t_c)}\right] = \quad [40]$$

$$-\gamma^2 D\left[\delta^2\left(4\Delta + 6\tau - \frac{2}{3}\delta\right)G_a^2 + 2\tau\delta(\delta_1 - \delta_2)G_a G_0 + \frac{4}{3}\tau^3 G_0^3\right]$$

for Condition I. As might be seen, the selection of $\delta_1 = \delta_2$ effectively eliminates the cross term $G_a G_0$. However, the thirteen interval sequence fails to eliminate the cross term:

$$\ln\left[\frac{m^{II}(G_a, t_c)}{m^{II}(0, t_c)}\right] = -\gamma^2 \quad [41]$$

$$D\left[\delta^2\left(4\Delta + 6\tau - \frac{2}{3}\delta\right)G_a^2 + \delta\left[\frac{\delta^2}{3} - \delta\tau - (\delta_1^2 - \delta_2^2)\right]G_a G_0 + \frac{4}{3}\tau^3 G_0^3\right]$$

However, the effect of this cross term may be minimized by the selection of the length of the gradient pulse.

While the 9 interval pulse sequence set forth in the paper does similarly eliminate or minimize the cross term, use of the 13 interval sequence assists in attenuation of the signal which is important for measurement of low diffusivities as may be seen where measuring gas and one experiences long $T_1$ times, despite the existence of relatively short $T_2$ times (See, Table 1, supra). A modification of a Carr Purcell PFG sequence such as the thirteen interval sequence may be utilized to not only suppress background gradients as may be seen downhole, but to provide additional information relating to the correlation of displacement and imaging. In Han, I. et al., *Two-Dimensional PFG NMR Encoding Correlations of Position, Velocity and Acceleration in Fluid Transport*, Journal of Magnetic Resonance vol. 146, pp. 169–180 (2000), techniques for encoding additional information that may be used to characterize the position, velocity and acceleration of flow are described. In imaging with phase encoding, these techniques can be extended to probe motion in more than one direction. Therein, it is suggested that the introduction of bipolar gradients stepped independent of the other may be used for the purposes of encoding information relative to the position and velocity of the particles in the flow. It will be appreciated that by being able to track motion in more than one direction, one may be able to determine the source of the fluid flow. When applied to a formation test tool, one may determine anisotropic permeability characteristics from the directional flow.

These concepts are generally referred to as POSXY (position exchange spectroscopy) and VESXY (velocity exchange spectroscopy).

Figure 25B:
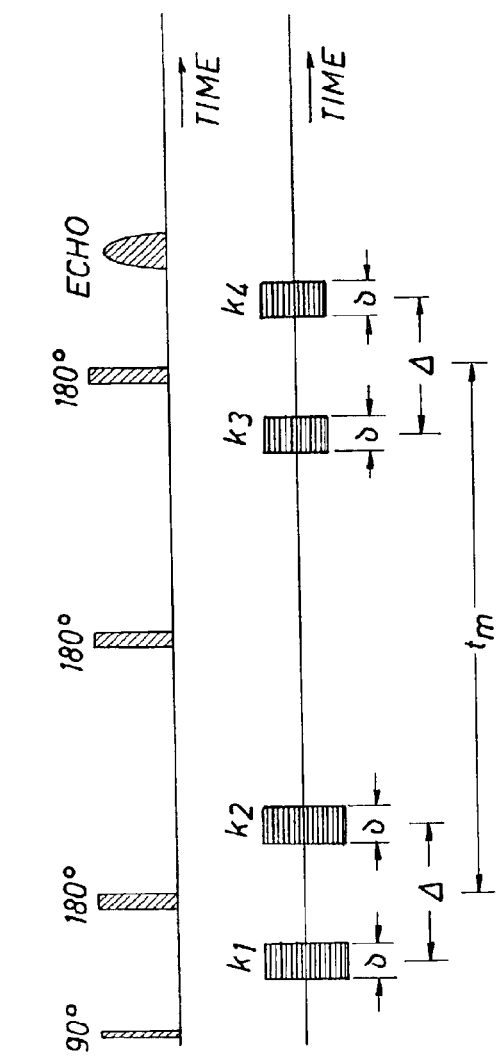

The POSXY technique encodes average position on the principal diagonal and position change corresponding to velocity on the secondary diagonal. In one technique, The gradients are stepped independently and are bipolar along the secondary diagonal such that $k_1 = -k_2$ resulting in a wave vector in q space. See FIG. 25a. Along the principal diagonal the two gradient pulses are unipolar so that $k = (k_1 + k_2)/2$ is represented corresponding to the average position between two time points t=0 and t=Δ. A 2D Fourier transformation permits one to correlate the displacement of the spin packets with the average position r parallel to the applied gradient direction. This can then be used to determine an average velocity of the spin packet by dividing the displacement by the elapsed time Δ. In VEXSY, the pulse sequence utilizes two independent bipolar gradient pulse pairs, each covering an equal "area" or intensity wherein $k_1 = -k_2$ and $k_3 = -k_4$. As noted therein, the application of a second set of gradient pulses $k_3$ and $k_4$ may be used to derive higher order derivatives, as acceleration of the flow. See FIG. 25B The first anti-phase pulse pairs are used to encode initial and final velocities resulting in average velocity along the principal diagonal fluctuating components of velocity or acceleration on the secondary diagonal.

Figure 26:
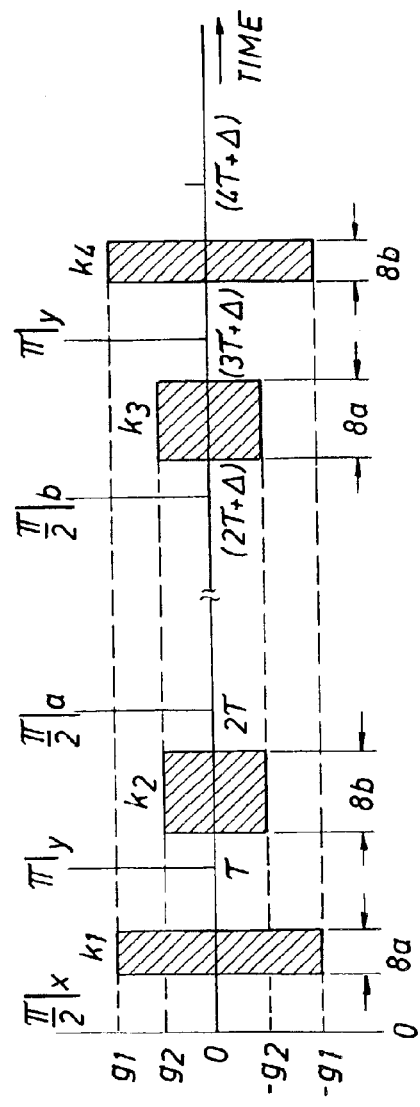
FIG. 26 is a depiction of an exemplary thirteen interval sequence utilizing bipolar pulsed field gradients.

The present invention may utilize the POSXY and VESXY techniques disclosed in the Han article in combination with the thirteen interval sequence. An exemplary proposed sequence of this type is depicted in FIG. 26. The sequence is similar to the conventional sequence depicted in FIG. 25a, with the exception of the nature of the applied pulsed field gradients. The first gradient pulse which encodes $k_1$, is stepped from between a range $G_1$ and $-G_2$ for a period of $\delta_a$, whereas the second one encoding $k_2$ is stepped between a range $G_2$ and $-G_2$ for a period of $\delta_b$. As noted in the Han article, the requirement is that the intensity of the gradient paid be such that $k_1 = -k_2$. Accordingly, the range for each of the pulses need not be the same so long as the intensity of the pulse is equal but negative. Pulsed gradients producing $k_3$ and $k_4$ are shown as having similar magnitudes and durations. While depicted as such in FIG. 26, it should be noted that while $k_1 = -k_2$, $k_3$ and $k_4$ need not be of the same intensity. The only requirement is that $k_3=-k_4$. The received signal intensity is then plotted two-dimensionally as a function of the area of the gradient pairs, $k_1$ and $k_2$, and $k_3$ and $k_4$, which permits one to determine the correlation spectrum of particle displacement, velocity with compensation of background gradients. Similarly, the VESXY experiment of FIG. 25*b* may be extended to background gradient compensation to yield a correlation spectrum of velocity and acceleration corresponding to the correlation of average velocity and diffusion broadening. FIG. 26 does not depict the selection of the polarization of the gradient pulses. The pulses may be selected such that $k_1$ is stepped by changing $-G_1$ to $G_1$ (a "−" pulse), while $k_2$ is stepped by changing $G_2$ to $-G_2$ (a "+" pulse). It is contemplated within the present invention that one could vary the sequence in which the gradient pulse pairs are applied. For example the pulse sequence could be +−+−, or −++−, or any sequence of positive and negative pulses so long as the gradient pulse produce pairs of equal but negative intensity with respect to each other. In summary when combined with the application of independent bipolar gradient pulses subsequent application of a 2-D Fourier transformation correlation centered around 180° RF pulses to replace original gradient pulses in POXSY and VEXSY, by spectra of fluid displacement, velocity, and acceleration in the formation as it flows into the snorkel of the formation tester can be obtained. Here the background gradient compensated POXSY experiment is a 2D version of the 13 interval sequence.

Further modifications may be made to the 13 interval sequence. For compensation of magnetization dephasing in quadratic fields, each gradient pulse of the original sequence is replaced by an antiphase pairs of antiphase gradient pulses involving two 180° RF pulses, where $k_1=-k_2=-k_3=k_4$ and $k_5=-k_6=-k_7=k_8$. FIG. 27. In a similar fashion the VESXY experiment of FIG. 25*b* for correlation of velocity and acceleration may be modified to account for compensation of linear, quadratic, and other non-linear background field profiles.

Conclusion

The present invention discloses various RF antenna—permanent magnet—EM coil structures that may be used to carry out pulsed field gradient experiments, including eccentered (near borehole wall) structures and borehole centered devices. The present invention discloses a means for directly determining permeability as a function of fluid flow images, including directional flow to determine anisotropic permeability. The present invention further discloses the application of various MRI imaging techniques that may be used to image the formation about the borehole for the disclosed structures. The present invention discloses means for creating azimuthally sensitive MRI images of the formation about the borehole. The present invention further discloses a means for inducing flow from the formation using a formation test tool and imaging the formation fluid characteristics and determining self-diffusion of the fluid. These MRI imaging techniques may be used in conjunction with known NMR logging techniques to determine porosity, permeability and determining the character of the fluids within the formation.

The present invention further discloses MRI imaging techniques that may be used in conjunction with test tools that induce flow from the formation into the borehole, thereby measuring formation flow rates and obtaining a more accurate determination of permeability of the formation.

While the present invention has been described in terms of various embodiments, modifications in the apparatus and techniques described herein without departing from the concept of the present invention. It should be understood that the embodiments and techniques described in the foregoing are illustrative and are not intended to operate as a limitation on the scope of the invention.

We claim:

1. A method for determining the permeability of a hydrocarbon bearing earth formation, the steps comprising:
   (a) locating a tool at a selected position in a borehole penetrating the earth formation;
   (b) inducing a flow of fluid within the earth formation to said tool;
   (c) creating at least two MRI images of said fluid while flowing within the earth formation to said tool, said at least two images being created at different times;
   (d) determining displacement of said fluid within the earth formation between relative to said different times; and
   (e) determining in situ the earth formation permeability from the displacement of said fluid.

2. A method for determining the permeability of a hydrocarbon bearing earth formation, the steps comprising:
   (a) locating a tool at a selected position in a borehole penetrating the earth formation;
   (b) inducing a flow of fluid within the earth formation to said tool;
   (c) creating at least two MRI images of said fluid while flowing within the earth formation to said tool utilizing a pulsed field gradient NMR experiment, said at least two MRI images being created at different times;
   (d) determining displacement of said fluid within the earth formation relative to said different times;
   (e) determining the in situ earth formation permeability from the displacement of said fluid.

3. The method of claim 1 or 2, wherein said step of inducing a flow of fluid further includes the steps of:
   (a) isolating the earth formation from the borehole;
   (b) creating a fluid flow channel from the earth formation to said tool; and
   (c) inducing a pressure differential between said tool and the earth formation.

4. The method of claim 1 or 2, wherein the step of creating said at least two MRI images, comprises creating said MRI images utilizing Time Of Flight angiography pulsed field gradient experiments to create said images.

5. The method of claim 1 or 2, wherein the step of creating said at least two MRI images further includes the steps of:
   (a) creating a static magnetic field in the earth formation to polarize and align selected nuclei within said fluid;
   (b) applying a 90° sinc radio frequency pulse and a first pulsed gradient magnetic field to the earth formation, said radio frequency pulse being applied perpendicular to said static magnetic field and said first pulsed gradient field being generally aligned with said static magnetic field;
   (c) applying a second and a third pulsed gradient magnetic field to the earth formation following termination of the radio frequency pulse and said first pulsed gradient magnetic field, and said first, second and third pulsed gradient magnetic fields being mutually orthogonal;
   (d) applying a 90° square radio frequency pulse to the earth formation;
   (e) applying the third pulsed field gradient again to the earth formation together with a second 90° sinc radio frequency pulse;
   (f) receiving a spin echo signal from said nuclei within said fluid;
   (g) creating an image from said signal; and
   (h) repeating steps (e)–(g) for each MRI image created.

6. The method of claim 1 or 2, wherein the step of creating said at least two MRI images comprises utilizing a pulsed gradient echo spin sequence to create said images.

7. The method of claim 1 or 2, wherein the step of creating said at least two MRI images further includes the steps of:
(a) applying a static magnetic field to the earth formation to polarize and align nuclei within said fluid within the earth formation;
(b) applying a 90° sinc radio frequency pulse and a slice selection gradient magnetic field to said fluid;
(c) applying a 180° square radio frequency pulse and a second slice selection gradient magnetic field to said fluid;
(d) applying a stepped phase gradient spin echo radio frequency pulse, following by a second 180° square radio frequency pulse to said fluid;
(e) applying a second and a third stepped phase gradient spin echo radio frequency pulse to said fluid;
(f) applying a stepped phase encoding magnetic field gradient pulse and a stepped frequency encoding magnetic field gradient pulse to said fluid;
(g) applying a fourth stepped phase gradient spin echo pulse to said fluid;
(h) applying a second stepped phase encoding magnetic field gradient pulse and a stepped frequency encoding magnetic field gradient pulse to said fluid;
(i) acquiring a spin echo signal from said nuclei during step (h);
(j) creating an image from said signal; and
(k) repeating steps (a)–(j) for each of said at least two MRI images.

8. The method of claim 1 or 2, further including the step of determining the anisotropic permeability of the earth formation.

9. The method of claim 8, wherein the step of determining the anisotropic permeability of the earth formation further includes the step of utilizing a modified Carr Purcell pulsed field gradient sequence to create said at least two MRI images.

10. The method of claim 9, wherein the step of utilizing a modified Carr Purcell pulsed field gradient includes the steps of:
(a) applying a static magnetic field to the earth formation to polarize and align nuclei within said fluid within the earth formation;
(b) applying a first 90° square radio frequency pulse to said fluid;
(c) applying a first negative stepped pulse field gradient to said fluid;
(d) applying a first 180° radio frequency pulse to said fluid;
(e) applying a first positive stepped pulse field gradient to said fluid, said gradient being equal in intensity to said first negative stepped pulse field gradient;
(f) applying a second 90° square radio frequency pulse to said fluid;
(g) applying a third 90° square radio frequency pulse to said fluid following a selected period of time;
(h) applying a second negative stepped pulse field gradient to said fluid;
(i) applying a second 180° radio frequency pulse to said fluid;
(j) applying a second positive stepped pulse field gradient to said fluid, said gradient being equal in intensity to said second negative stepped pulse field gradient;
(k) acquiring spin echo signals from the nuclei during steps (h)–(j);
(l) creating an image from said signals, said image being indicative of a position and flow direction of said fluid; and
(m) repeating steps (b)–(l) for each of said at least two MRI images.

11. The method of claim 8, wherein the step of creating said at least two MRI images further includes the step of utilizing a modified Carr Purcell pulsed bipolar field gradient pair sequence to create said at least two MRI images.

12. The method of claim 11, wherein the step of utilizing a modified Carr Purcell bipolar pulsed field gradient includes the steps of:
(a) applying a static magnetic field to the earth formation to polarize and align nuclei within said fluid within the earth formation;
(b) applying a first 90° square radio frequency pulse to said fluid;
(c) applying a first bipolar stepped pulse field gradient to said fluid, said gradient being stepped in a first selected direction;
(d) applying a first 180° radio frequency pulse to said fluid;
(e) applying a second bipolar stepped pulse field gradient to said fluid, said gradient being equal in intensity to said first bipolar stepped pulse field gradient and stepped in a direction opposite to said first selected direction;
(f) applying a second 90° square radio frequency pulse to said fluid;
(g) applying a third 90° square radio frequency pulse to said fluid following a selected period of time;
(h) applying a third bipolar stepped pulse field gradient to said fluid, said gradient being stepped in a second selected direction;
(i) applying a second 180° radio frequency pulse to said fluid;
(j) applying a fourth bipolar stepped pulse field gradient to said fluid, said gradient being equal in intensity to said third bipolar stepped pulse field gradient and stepped in a direction opposite to said second selected direction;
(k) acquiring spin echo signals from the nuclei during steps (h)–(j);
(l) creating an image from said signals, said image being indicative of a position and flow direction of said fluid; and
(m) repeating steps (b)–(l) for each of said at least two MRI images.

13. The method of claim 2, further including the steps of:
(a) performing at least one CPMG NMR experiment on the earth formation and said fluid as said fluid flows to said tool;
(b) receiving a spin echo signal from said fluid following said at least one CPMG NMR experiment; and
(c) determining one or more petrophysical properties related to the earth formation or said fluid.

14. The method of claim 13, wherein the petrophysical properties determined include the earth formation porosity.

15. The method of claim 13, wherein the petrophyscial properties determined include bulk volume free and irreducible water in the earth formation.

16. The method of claim 13, wherein the petrophysical properties determined include said fluid viscosity.

17. The method of claim 13, wherein the petrophysical properties determined include determining types of hydrocarbons present in said fluid.

* * * * *